(12) United States Patent
Zhang et al.

(10) Patent No.: US 12,258,408 B2
(45) Date of Patent: Mar. 25, 2025

(54) ONCOLYTIC VIRUS EXPRESSING PD-1 BINDING PROTEIN AND APPLICATION OF ONCOLYTIC VIRUS

(71) Applicant: SHANGHAI YUANSONG BIOTECHNOLOGY CO. LTD., Shanghai (CN)

(72) Inventors: Kangjian Zhang, Shanghai (CN); Xianlong Fang, Shanghai (CN); Jinfa Gu, Shanghai (CN); Xinyuan Liu, Shanghai (CN)

(73) Assignee: SHANGHAI YUANSONG BIOTECHNOLOGY CO. LTD., Shanghai (CN)

( * ) Notice: Subject to any disclaimer, the term of this patent is extended or adjusted under 35 U.S.C. 154(b) by 937 days.

(21) Appl. No.: 17/288,006

(22) PCT Filed: Oct. 24, 2019

(86) PCT No.: PCT/CN2019/112905
§ 371 (c)(1),
(2) Date: Apr. 23, 2021

(87) PCT Pub. No.: WO2020/083324
PCT Pub. Date: Apr. 30, 2020

(65) Prior Publication Data
US 2021/0403564 A1  Dec. 30, 2021

(30) Foreign Application Priority Data
Oct. 26, 2018  (CN) .................. 201811259785.9

(51) Int. Cl.
| | |
|---|---|
| C07K 16/28 | (2006.01) |
| A61K 39/00 | (2006.01) |
| A61P 35/00 | (2006.01) |
| C12N 7/00 | (2006.01) |
| C12N 15/86 | (2006.01) |

(52) U.S. Cl.
CPC .......... *C07K 16/2818* (2013.01); *A61K 39/00* (2013.01); *A61P 35/00* (2018.01); *C12N 7/00* (2013.01); *A61K 2039/505* (2013.01); *A61K 2039/545* (2013.01); *C07K 2317/52* (2013.01); *C07K 2317/565* (2013.01); *C07K 2317/622* (2013.01); *C07K 2319/02* (2013.01); *C07K 2319/30* (2013.01); *C12N 2710/10021* (2013.01); *C12N 2710/10032* (2013.01)

(58) Field of Classification Search
CPC .......... C07K 16/2818; C07K 2317/52; C07K 2317/565; C07K 2317/622; C07K 2319/02; C07K 2319/30; C07K 2317/56; C07K 2317/64; C07K 2317/73; C07K 2317/76; A61P 35/00; C12N 7/00; C12N 2710/10021; C12N 2710/10032; C12N 15/86; C12N 2710/10321; C12N 2710/10343; A61K 2039/505; A61K 2039/545; A61K 2039/53; A61K 35/761; A61K 39/00; Y02A 50/30
See application file for complete search history.

(56) References Cited

U.S. PATENT DOCUMENTS

| | | | |
|---|---|---|---|
| 2015/0250837 A1* | 9/2015 | Nolin ............... | A61K 35/761 |
| | | | 435/235.1 |
| 2017/0044260 A1 | 2/2017 | Baruah et al. | |
| 2017/0157188 A1 | 6/2017 | Silvestre et al. | |
| 2018/0346569 A1 | 12/2018 | Wang et al. | |

FOREIGN PATENT DOCUMENTS

| | | | |
|---|---|---|---|
| CN | 105111314 A | 12/2015 | |
| CN | 106699889 A | 5/2017 | |
| CN | 107208069 A | 9/2017 | |
| CN | 108064305 A | 5/2018 | |
| CN | 108342366 A | 7/2018 | |
| CN | 108473977 A | 8/2018 | |
| WO | WO-2017087599 A1 * | 5/2017 | ............. A61P 35/00 |
| WO | 2018167320 A1 | 9/2018 | |

OTHER PUBLICATIONS

International Search Report for PCT/CN2019/112905 mailed Feb. 1, 2020, ISA/CN.
Yan,Zejun et al. Construction and identification of a recombinant adenoviral vector with Survivin promoter. Modern Practical Medicine, vol. 24, No. (6),Jun. 30, 2012 ISSN: 1671-0800, pp. 607-609, see entire document.
Robert M. Lorence,Complete Regression of Human Fibrosarcoma Xenografts after Local Newcastle Disease Virus Therapy,Cancer Research 54, 6017-6021, Dec. 1, 1994.
Matthew C. Coffey,Reovirus Therapy of Tumors with Activated Ras Pathway, www.sciencemag.org, Science vol. 282, Nov. 13, 1998, 1332-1334.
David Kirn,Replication-selective virotherapy for cancer: Biological principles, risk management and future directions, Nature Medicine,vol. 7,No. 7 ,Jul. 2001,781-787.
Kah-Whye Peng,Systemic therapy of myeloma xenografts by an attenuated measles virus,Blood, Oct. 1, 2001, vol. 98, No. 7,2002-2007.

(Continued)

*Primary Examiner* — Janet L Andres
*Assistant Examiner* — Samadhan Jaising Jadhao
(74) *Attorney, Agent, or Firm* — Yue (Robert) Xu; Apex Attorneys at Law, LLP

(57) ABSTRACT

Provided is an oncolytic virus expressing a PD-1 binding protein, i.e., an oncolytic adenovirus comprising a fusion protein expressing a PD-1 single-chain antibody, wherein the fusion protein has a structure of S-$V_L$-L-$V_H$-Fc, S is an optional signal peptide sequence, $V_L$ is the light chain variable region of the PD-1 single-chain antibody, L is a flexible linker, $V_H$ is the heavy chain variable region of the PD-1 single-chain antibody and Fc is an immunoglobulin Fc fragment.

18 Claims, 9 Drawing Sheets

Specification includes a Sequence Listing.

(56) References Cited

OTHER PUBLICATIONS

Mol Ther, Stacy J Kowalsky, Superagonist IL-15-Armed Oncolytic Virus Elicits Potent Antitumor Immunity and Therapy That Are Enhanced with PD-1 Blockade, pp. 2476-2486, Oct. 3, 2018.

* cited by examiner

A

B

A

B

A

B

C

SEQUENCE LISTING

```
<160> NUMBER OF SEQ ID NOS: 22

<210> SEQ ID NO 1
<211> LENGTH: 235
<212> TYPE: PRT
<213> ORGANISM: Artificial Sequence
<220> FEATURE:
<223> OTHER INFORMATION: Light Chain Sequence of PD-1 Antibody

<400> SEQUENCE: 1

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Gly
        35                  40                  45

Gln Asn Val Gln Asn Tyr Leu Ala Trp Tyr Gln Gln Lys Pro Gly Lys
    50                  55                  60

Ala Pro Lys Val Leu Ile Phe Asn Ala Gln Ser Leu Gln Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Trp Pro Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 2
<211> LENGTH: 470
<212> TYPE: PRT
<213> ORGANISM: Artificial Sequence
<220> FEATURE:
<223> OTHER INFORMATION: Heavy Chain Sequence of PD-1 Antibody

<400> SEQUENCE: 2
```

-continued

```
Met Asp Met Arg Val Pro Ala Gln Leu Leu Gly Leu Leu Leu Trp
1               5                   10                  15

Leu Pro Gly Ala Arg Cys Gln Val Thr Leu Lys Glu Ser Gly Pro Ala
            20                  25                  30

Leu Val Lys Pro Thr Gln Thr Leu Thr Leu Thr Cys Thr Phe Ser Gly
            35                  40                  45

Phe Ser Leu Ser Thr Ser Gly Thr Cys Val Ser Trp Ile Arg Gln Pro
50                  55                  60

Pro Gly Lys Ala Leu Glu Trp Leu Ala Thr Ile Cys Trp Glu Asp Ser
65                  70                  75                  80

Lys Gly Tyr Ser Thr Ser Leu Lys Ser Arg Leu Thr Ile Ser Lys Asp
            85                  90                  95

Thr Ser Lys Asn Gln Ala Val Leu Thr Met Thr Asn Met Asp Pro Val
            100                 105                 110

Asp Thr Ala Thr Tyr Tyr Cys Ala Arg Arg Glu Asp Ser Gly Tyr Phe
            115                 120                 125

Trp Phe Pro Tyr Trp Gly Gln Gly Thr Leu Val Thr Val Ser Ser Ala
130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Lys Thr Tyr
210                 215                 220

Thr Cys Asn Val Asp His Lys Pro Ser Asn Thr Lys Val Asp Lys Arg
225                 230                 235                 240

Val Glu Ser Lys Tyr Gly Pro Pro Cys Pro Pro Cys Pro Ala Pro Glu
            245                 250                 255

Phe Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser Gln Glu Asp Pro Glu Val Gln Phe Asn Trp Tyr Val Asp Gly
            290                 295                 300

Val Glu Val His Asn Ala Lys Thr Lys Pro Arg Glu Glu Gln Phe Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Gly Leu Pro
            340                 345                 350

Ser Ser Ile Glu Lys Thr Ile Ser Lys Ala Lys Gly Gln Pro Arg Glu
            355                 360                 365

Pro Gln Val Tyr Thr Leu Pro Pro Ser Gln Glu Glu Met Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415
```

```
Thr Pro Pro Val Leu Asp Ser Asp Gly Ser Phe Phe Leu Tyr Ser Arg
            420                 425                 430

Leu Thr Val Asp Lys Ser Arg Trp Gln Glu Gly Asn Val Phe Ser Cys
            435                 440                 445

Ser Val Met His Glu Ala Leu His Asn His Tyr Thr Gln Lys Ser Leu
        450                 455                 460

Ser Leu Ser Leu Gly Lys
465             470

<210> SEQ ID NO 3
<211> LENGTH: 121
<212> TYPE: PRT
<213> ORGANISM: Artificial Sequence
<220> FEATURE:
<223> OTHER INFORMATION: Heavy chain variable region

<400> SEQUENCE: 3

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Thr Cys Val Ser Trp Ile Arg Gln Pro Pro Gly Lys Ala Leu Glu
        35                  40                  45

Trp Leu Ala Thr Ile Cys Trp Glu Asp Ser Lys Gly Tyr Ser Thr Ser
    50                  55                  60

Leu Lys Ser Arg Leu Thr Ile Ser Lys Asp Thr Ser Lys Asn Gln Ala
65                  70                  75                  80

Val Leu Thr Met Thr Asn Met Asp Pro Val Asp Thr Ala Thr Tyr Tyr
            85                  90                  95

Cys Ala Arg Arg Glu Asp Ser Gly Tyr Phe Trp Phe Pro Tyr Trp Gly
        100                 105                 110

Gln Gly Thr Leu Val Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: Light chain variable region

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Asn Val Gln Asn Tyr
            20                  25                  30

Leu Ala Trp Tyr Gln Gln Lys Pro Gly Lys Ala Pro Lys Val Leu Ile
        35                  40                  45

Phe Asn Ala Gln Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Trp Pro Thr
            85                  90                  95

Phe Gly Gly Gly Thr Lys Val Glu Ile Lys
        100                 105

<210> SEQ ID NO 5
```

```
<211> LENGTH: 279
<212> TYPE: PRT
<213> ORGANISM: Artificial Sequence
<220> FEATURE:
<223> OTHER INFORMATION: Amino acid sequence of the single-chain
      antibody

<400> SEQUENCE: 5

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Gly
        35                  40                  45

Gln Asn Val Gln Asn Tyr Leu Ala Trp Tyr Gln Gln Lys Pro Gly Lys
    50                  55                  60

Ala Pro Lys Val Leu Ile Phe Asn Ala Gln Ser Leu Gln Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Trp Pro Thr Phe Gly Gly Gly Thr Lys Val Glu Ile Lys
        115                 120                 125

Gly Gly Gly Gly Ser Gly Gly Gly Ser Gly Gly Gly Ser Gly
    130                 135                 140

Gly Gly Ser Gly Gly Gly Ser Gly Gly Gly Ser Gln Val
145                 150                 155                 160

Thr Leu Lys Glu Ser Gly Pro Ala Leu Val Lys Pro Thr Gln Thr Leu
                165                 170                 175

Thr Leu Thr Cys Thr Phe Ser Gly Phe Ser Leu Ser Thr Ser Gly Thr
            180                 185                 190

Cys Val Ser Trp Ile Arg Gln Pro Pro Gly Lys Ala Leu Glu Trp Leu
        195                 200                 205

Ala Thr Ile Cys Trp Glu Asp Ser Lys Gly Tyr Ser Thr Ser Leu Lys
    210                 215                 220

Ser Arg Leu Thr Ile Ser Lys Asp Thr Ser Lys Asn Gln Ala Val Leu
225                 230                 235                 240

Thr Met Thr Asn Met Asp Pro Val Asp Thr Ala Thr Tyr Tyr Cys Ala
                245                 250                 255

Arg Arg Glu Asp Ser Gly Tyr Phe Trp Phe Pro Tyr Trp Gly Gln Gly
            260                 265                 270

Thr Leu Val Thr Val Ser Ser
        275

<210> SEQ ID NO 6
<211> LENGTH: 840
<212> TYPE: DNA
<213> ORGANISM: Artificial Sequence
<220> FEATURE:
<223> OTHER INFORMATION: Coding sequence of the single-chain antibody

<400> SEQUENCE: 6
atggatatga gagtaccagc tcagctgctg ggcctgctgc tcctgtggtt ccctggcagc        60
cggtgcgaca tccagatgac gcagagcccc tccagtctct ctgctagcgt gggcgacagg       120
gtcacaatta catgcagagc tggacagaac gtccagaatt atttggcctg gtaccagcag       180
```

```
aaacctggaa aggctccaaa ggtgttgatc ttcaatgcgc aatctctcca acaggcgtg      240 ccctcccgct tctccggctc agggtctggc accgactta  cccttaccat ctctagcctt     300
cagcctgagg attttgctac ttactactgt cagcagtata attcctggcc tacatttggt     360
ggtggtacga aagtcgagat taagggtggt ggaggttctg gaggaggtgg aagtggtggc     420
ggaggaagcg gcggtggtgg ttcaggaggg ggagggtcag ggggggggagg ctcccaagtt    480 acactcaagg aaagcggtcc ggcccttgta aagcccaccc agacactgac tctgacctgt     540
acattcagcg gcttcagcct gtcaacgtcc ggcacatgtg ttagctggat acgccagccc     600
ccggggaaag cactggagtg gctcgcgacc atctgctggg aagatagtaa agggtactct     660
acaagcctta aatcacgcct gaccatttca aaggatacta gtaagaatca ggccgtcctt     720
acaatgacca atatggatcc cgtcgacact gcaacatact attgtgcccg ccgggaagat     780
agcggatact tctggttccc ctactggggc caaggaactc tcgtgacagt cagttcctaa    840
```

<210> SEQ ID NO 7
<211> LENGTH: 279
<212> TYPE: PRT
<213> ORGANISM: Artificial Sequence
<220> FEATURE:
<223> OTHER INFORMATION: Amino acid sequence of the single-chain antibody

<400> SEQUENCE: 7

```
Met Asp Met Arg Val Pro Ala Gln Leu Leu Gly Leu Leu Leu Leu Trp
1               5                   10                  15

Leu Pro Gly Ala Arg Cys Gln Val Thr Leu Lys Glu Ser Gly Pro Ala
            20                  25                  30

Leu Val Lys Pro Thr Gln Thr Leu Thr Leu Thr Cys Thr Phe Ser Gly
        35                  40                  45

Phe Ser Leu Ser Thr Ser Gly Thr Cys Val Ser Trp Ile Arg Gln Pro
    50                  55                  60

Pro Gly Lys Ala Leu Glu Trp Leu Ala Thr Ile Cys Trp Glu Asp Ser
65                  70                  75                  80

Lys Gly Tyr Ser Thr Ser Leu Lys Ser Arg Leu Thr Ile Ser Lys Asp
                85                  90                  95

Thr Ser Lys Asn Gln Ala Val Leu Thr Met Thr Asn Met Asp Pro Val
            100                 105                 110

Asp Thr Ala Thr Tyr Tyr Cys Ala Arg Arg Glu Asp Ser Gly Tyr Phe
        115                 120                 125

Trp Phe Pro Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Gly Gly
145                 150                 155                 160

Gly Gly Ser Gly Gly Gly Gly Ser Gly Gly Gly Ser Asp Ile Gln
                165                 170                 175

Met Thr Gln Ser Pro Ser Ser Leu Ser Ala Ser Val Gly Asp Arg Val
            180                 185                 190

Thr Ile Thr Cys Arg Ala Gly Gln Asn Val Gln Asn Tyr Leu Ala Trp
        195                 200                 205

Tyr Gln Gln Lys Pro Gly Lys Ala Pro Lys Val Leu Ile Phe Asn Ala
    210                 215                 220

Gln Ser Leu Gln Thr Gly Val Pro Ser Arg Phe Ser Gly Ser Gly Ser
225                 230                 235                 240

Gly Thr Asp Phe Thr Leu Thr Ile Ser Ser Leu Gln Pro Glu Asp Phe
```

```
                245                 250                 255
Ala Thr Tyr Tyr Cys Gln Gln Tyr Asn Ser Trp Pro Thr Phe Gly Gly
            260                 265                 270

Gly Thr Lys Val Glu Ile Lys
        275

<210> SEQ ID NO 8
<211> LENGTH: 840
<212> TYPE: DNA
<213> ORGANISM: Artificial Sequence
<220> FEATURE:
<223> OTHER INFORMATION: Coding sequence of the single-chain antibody

<400> SEQUENCE: 8
atggacatga gagtcccagc ccagctgctt ggtctgttgc ttctctggct cccgggtgcc      60
cgctgccagg tgacgctgaa ggagtcaggc cctgccttgg ttaagcccac ccagaccctg     120
accctcacat gtaccttctc cgggttctca ttgtcaacct ccggcacttg tgtcagttgg     180
atcaggcaac cccctggcaa agcccttgag tggttggcta cgatttgctg ggaagacagt     240
aaaggatact caacaagcct caaatctcgg ctgaccatta gtaaagatac atccaagaac     300
caggcagtcc ttaccatgac caatatggac ccagtcgata ccgccaccta ctattgcgct     360
cgccgagagg attctggcta cttctggttc ccatattggg gccaaggaac acttgtgacc     420
gtatcaagtg gtggaggggg tagcggtgga ggtggaagtg gtggcggagg aagtggcgga     480
ggtgggtccg gaggcggcgg ctccggagga ggtggttcag atattcagat gacccagtcc     540
cccagctctc tgagtgcatc cgtcggcgat agagtgacta tcacatgtcg agccggacag     600
aacgtgcaaa attacctggc ctggtaccag cagaagccgg gtaaggctcc caaagtgctt     660
attttcaatg cccaatctct gcagaccggg gtgccaagcc ggtttagtgg ttctggctcc     720
ggtactgact tcacgcttac catttccagt ctgcaaccgg aggatttcgc tacatattac     780
tgccagcagt acaacagctg gccaaccttc gggggcggga caaaagttga aatcaagtaa     840

<210> SEQ ID NO 9
<211> LENGTH: 327
<212> TYPE: PRT
<213> ORGANISM: Artificial Sequence
<220> FEATURE:
<223> OTHER INFORMATION: Fc fragment

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125
```

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 10
<211> LENGTH: 606
<212> TYPE: PRT
<213> ORGANISM: Artificial Sequence
<220> FEATURE:
<223> OTHER INFORMATION: Single-chain antibody fused with the Fc
      fragment

<400> SEQUENCE: 10

Met Asp Met Arg Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
            20                  25                  30

Leu Ser Ala Ser Val Gly Asp Arg Val Thr Ile Thr Cys Arg Ala Gly
        35                  40                  45

Gln Asn Val Gln Asn Tyr Leu Ala Trp Tyr Gln Gln Lys Pro Gly Lys
    50                  55                  60

Ala Pro Lys Val Leu Ile Phe Asn Ala Gln Ser Leu Gln Thr Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Trp Pro Thr Phe Gly Gly Gly Thr Lys Val Glu Ile Lys
        115                 120                 125

Gly Gly Gly Gly Ser Gly Gly Gly Ser Gly Gly Gly Gly Ser Gly
    130                 135                 140

Gly Gly Gly Ser Gly Gly Gly Gly Ser Gly Gly Gly Gly Ser Gln Val

```
            145                 150                 155                 160
        Thr Leu Lys Glu Ser Gly Pro Ala Leu Val Lys Pro Thr Gln Thr Leu
                        165                 170                 175

Thr Leu Thr Cys Thr Phe Ser Gly Phe Ser Leu Ser Thr Ser Gly Thr
                        180                 185                 190

Cys Val Ser Trp Ile Arg Gln Pro Pro Gly Lys Ala Leu Glu Trp Leu
                        195                 200                 205

Ala Thr Ile Cys Trp Glu Asp Ser Lys Gly Tyr Ser Thr Ser Leu Lys
        210                 215                 220

Ser Arg Leu Thr Ile Ser Lys Asp Thr Ser Lys Asn Gln Ala Val Leu
        225                 230                 235                 240

Thr Met Thr Asn Met Asp Pro Val Asp Thr Ala Thr Tyr Tyr Cys Ala
                        245                 250                 255

Arg Arg Glu Asp Ser Gly Tyr Phe Trp Phe Pro Tyr Trp Gly Gln Gly
                        260                 265                 270

Thr Leu Val Thr Val Ser Ser Ala Ser Thr Lys Gly Pro Ser Val Phe
                        275                 280                 285

Pro Leu Ala Pro Cys Ser Arg Ser Thr Ser Glu Ser Thr Ala Ala Leu
                        290                 295                 300

Gly Cys Leu Val Lys Asp Tyr Phe Pro Glu Pro Val Thr Val Ser Trp
        305                 310                 315                 320

Asn Ser Gly Ala Leu Thr Ser Gly Val His Thr Phe Pro Ala Val Leu
                        325                 330                 335

Gln Ser Ser Gly Leu Tyr Ser Leu Ser Ser Val Val Thr Val Pro Ser
                        340                 345                 350

Ser Ser Leu Gly Thr Lys Thr Tyr Thr Cys Asn Val Asp His Lys Pro
                        355                 360                 365

Ser Asn Thr Lys Val Asp Lys Arg Val Glu Ser Lys Tyr Gly Pro Pro
                        370                 375                 380

Cys Pro Pro Cys Pro Ala Pro Glu Phe Leu Gly Gly Pro Ser Val Phe
        385                 390                 395                 400

Leu Phe Pro Pro Lys Pro Lys Asp Thr Leu Met Ile Ser Arg Thr Pro
                        405                 410                 415

Glu Val Thr Cys Val Val Val Asp Val Ser Gln Glu Asp Pro Glu Val
                        420                 425                 430

Gln Phe Asn Trp Tyr Val Asp Gly Val Glu Val His Asn Ala Lys Thr
                        435                 440                 445

Lys Pro Arg Glu Glu Gln Phe Asn Ser Thr Tyr Arg Val Val Ser Val
        450                 455                 460

Leu Thr Val Leu His Gln Asp Trp Leu Asn Gly Lys Glu Tyr Lys Cys
        465                 470                 475                 480

Lys Val Ser Asn Lys Gly Leu Pro Ser Ser Ile Glu Lys Thr Ile Ser
                        485                 490                 495

Lys Ala Lys Gly Gln Pro Arg Glu Pro Gln Val Tyr Thr Leu Pro Pro
                        500                 505                 510

Ser Gln Glu Glu Met Thr Lys Asn Gln Val Ser Leu Thr Cys Leu Val
                        515                 520                 525

Lys Gly Phe Tyr Pro Ser Asp Ile Ala Val Glu Trp Glu Ser Asn Gly
                        530                 535                 540

Gln Pro Glu Asn Asn Tyr Lys Thr Thr Pro Pro Val Leu Asp Ser Asp
        545                 550                 555                 560

Gly Ser Phe Phe Leu Tyr Ser Arg Leu Thr Val Asp Lys Ser Arg Trp
                        565                 570                 575
```

Gln Glu Gly Asn Val Phe Ser Cys Ser Val Met His Glu Ala Leu His
            580                 585                 590

Asn His Tyr Thr Gln Lys Ser Leu Ser Leu Ser Leu Gly Lys
            595                 600                 605

<210> SEQ ID NO 11
<211> LENGTH: 1821
<212> TYPE: DNA
<213> ORGANISM: Artificial Sequence
<220> FEATURE:
<223> OTHER INFORMATION: Coding sequence of single-chain antibody fused
      with the Fc fragment

<400> SEQUENCE: 11

| | | | | |
|---|---|---|---|---|
| atggatatgc | gggtgccggc | acagctgttg | gggctgctgc | tcctctggtt | tcctggctca | 60 |
| cgctgcgata | tccagatgac | tcagagtccc | agttccctgt | ctgcctctgt | gggcgataga | 120 |
| gtcaccataa | cctgtcgcgc | cggacaaaac | gtccaaaatt | acctggcgtg | gtaccagcag | 180 |
| aaaccaggaa | aggccccaaa | ggtcctgatt | ttcaatgctc | aaagcctcca | gactggagtc | 240 |
| cccagccggt | tctctggctc | cggatctggc | accgactttta | ccttgaccat | cagcagcctg | 300 |
| cagcccgagg | atttcgcaac | ctactattgt | cagcagtata | taagctggcc | aacattcggg | 360 |
| ggcggcacta | agtcgagat | caagggtgga | ggaggctctg | gtggcggggg | ctcaggggga | 420 |
| ggaggaagcg | gtggcggtgg | ttctggcgga | ggtggcagtg | gtggtggcgg | tagccaagta | 480 |
| accttgaagg | agtccggtcc | cgcactggtg | aaaccacac | aaacgcttac | gctcacttgt | 540 |
| accttcagcg | gttttagcct | gtctacgtcc | ggaacctgcg | tttcttggat | ccggcagcct | 600 |
| cccggcaagg | ccctcgagtg | gctggccacc | atctgctggg | aagactccaa | aggttactca | 660 |
| accagtctta | aaagtaggtt | gacaatcagc | aaggatacca | gtaaaaatca | ggcagttctt | 720 |
| accatgacaa | acatggatcc | cgtagataca | gctacctact | attgtgccag | cgagaagac | 780 |
| tccggttact | tttggttccc | ctactggggt | caggggactc | tggtcaccgt | cagctctgcc | 840 |
| tccaccaagg | gcccttctgt | gttccccctg | gcaccatgta | gccggtccac | ctccgagagc | 900 |
| actgcagcgt | gggctgctt | ggtgaaagac | tatttttccg | agcctgtaac | tgtgagttgg | 960 |
| aacagcggcg | ccctcacgag | cggggtgcac | acctttccg | cagtcttgca | gagctccggt | 1020 |
| ctctattccc | tttctagtgt | tgttaccgtg | ccgagcagct | ctcttggcac | caagacttac | 1080 |
| acctgcaatg | ttgaccataa | accgtctaat | actaaagttg | acaagagggt | cgagagcaaa | 1140 |
| tacgcccac | catgcccacc | ttgcccagca | cctgagttcc | tgggcggccc | ctcagtgttc | 1200 |
| ttgtttcccc | caaagcctaa | agacaccctg | atgattagcc | gcacaccga | ggtgacttgc | 1260 |
| gtcgtggtcg | atgtgagtca | ggaagaccct | gaagtgcagt | tcaactggta | tgtagacggg | 1320 |
| gttgaggtac | acaacgcaaa | gactaaacca | cgcgaggaac | agtttaatag | tacgtaccgg | 1380 |
| gtggtgtccg | tgcttacagt | cctgcaccag | gattggttga | atggaaagga | atataagtgc | 1440 |
| aaagtgagca | taaaggcct | gccttcttct | atcgagaaga | caatatccaa | agcaaaaggt | 1500 |
| caacctcggg | agcctcaggt | gtataccttg | cccccgagcc | aggaggaaat | gacgaaaaat | 1560 |
| caggttagtc | tgacgtgtct | tgtgaagggc | ttttacccat | ctgatatcgc | agtggagtgg | 1620 |
| gaaagcaacg | ggcagcccga | gaataactat | aagacgaccc | cgcccgtcct | ggactcagat | 1680 |
| ggtagcttct | tcctgtattc | ccgcctgaca | gttgacaaat | ctcgctggca | agaaggaaat | 1740 |
| gttttttcct | gcagtgtcat | gcatgaagcc | ctgcacaacc | attacacaca | gaaaagcttg | 1800 |
| agcctgagtc | tggggaagtg | a | | | | 1821 |

<210> SEQ ID NO 12
<211> LENGTH: 606
<212> TYPE: PRT
<213> ORGANISM: Artificial Sequence
<220> FEATURE:
<223> OTHER INFORMATION: Single-chain antibody fused with the Fc fragment

<400> SEQUENCE: 12

```
Met Asp Met Arg Val Pro Ala Gln Leu Leu Gly Leu Leu Leu Leu Trp
1               5                   10                  15

Leu Pro Gly Ala Arg Cys Gln Val Thr Leu Lys Glu Ser Gly Pro Ala
            20                  25                  30

Leu Val Lys Pro Thr Gln Thr Leu Thr Leu Thr Cys Thr Phe Ser Gly
        35                  40                  45

Phe Ser Leu Ser Thr Ser Gly Thr Cys Val Ser Trp Ile Arg Gln Pro
    50                  55                  60

Pro Gly Lys Ala Leu Glu Trp Leu Ala Thr Ile Cys Trp Glu Asp Ser
65                  70                  75                  80

Lys Gly Tyr Ser Thr Ser Leu Lys Ser Arg Leu Thr Ile Ser Lys Asp
                85                  90                  95

Thr Ser Lys Asn Gln Ala Val Leu Thr Met Thr Asn Met Asp Pro Val
            100                 105                 110

Asp Thr Ala Thr Tyr Tyr Cys Ala Arg Arg Glu Asp Ser Gly Tyr Phe
        115                 120                 125

Trp Phe Pro Tyr Trp Gly Gln Gly Thr Leu Val Thr Val Ser Ser Gly
    130                 135                 140

Gly Gly Gly Ser Gly Gly Gly Ser Gly Gly Gly Ser Gly Gly
145                 150                 155                 160

Gly Gly Ser Gly Gly Gly Ser Gly Gly Gly Ser Asp Ile Gln
                165                 170                 175

Met Thr Gln Ser Pro Ser Ser Leu Ser Ala Ser Val Gly Asp Arg Val
            180                 185                 190

Thr Ile Thr Cys Arg Ala Gly Gln Asn Val Gln Asn Tyr Leu Ala Trp
        195                 200                 205

Tyr Gln Gln Lys Pro Gly Lys Ala Pro Lys Val Leu Ile Phe Asn Ala
    210                 215                 220

Gln Ser Leu Gln Thr Gly Val Pro Ser Arg Phe Ser Gly Ser Gly Ser
225                 230                 235                 240

Gly Thr Asp Phe Thr Leu Thr Ile Ser Ser Leu Gln Pro Glu Asp Phe
                245                 250                 255

Ala Thr Tyr Tyr Cys Gln Gln Tyr Asn Ser Trp Pro Thr Phe Gly Gly
            260                 265                 270

Gly Thr Lys Val Glu Ile Lys Ala Ser Thr Lys Gly Pro Ser Val Phe
        275                 280                 285

Pro Leu Ala Pro Cys Ser Arg Ser Thr Ser Glu Ser Thr Ala Ala Leu
    290                 295                 300

Gly Cys Leu Val Lys Asp Tyr Phe Pro Glu Pro Val Thr Val Ser Trp
305                 310                 315                 320

Asn Ser Gly Ala Leu Thr Ser Gly Val His Thr Phe Pro Ala Val Leu
                325                 330                 335

Gln Ser Ser Gly Leu Tyr Ser Leu Ser Ser Val Val Thr Val Pro Ser
            340                 345                 350

Ser Ser Leu Gly Thr Lys Thr Tyr Thr Cys Asn Val Asp His Lys Pro
```

```
                355                 360                 365
Ser Asn Thr Lys Val Asp Lys Arg Val Glu Ser Lys Tyr Gly Pro Pro
        370                 375                 380
Cys Pro Cys Pro Ala Pro Glu Phe Leu Gly Gly Pro Ser Val Phe
385                 390                 395                 400
Leu Phe Pro Pro Lys Pro Lys Asp Thr Leu Met Ile Ser Arg Thr Pro
                405                 410                 415
Glu Val Thr Cys Val Val Val Asp Val Ser Gln Glu Asp Pro Glu Val
            420                 425                 430
Gln Phe Asn Trp Tyr Val Asp Gly Val Glu Val His Asn Ala Lys Thr
        435                 440                 445
Lys Pro Arg Glu Glu Gln Phe Asn Ser Thr Tyr Arg Val Val Ser Val
        450                 455                 460
Leu Thr Val Leu His Gln Asp Trp Leu Asn Gly Lys Glu Tyr Lys Cys
465                 470                 475                 480
Lys Val Ser Asn Lys Gly Leu Pro Ser Ser Ile Glu Lys Thr Ile Ser
                485                 490                 495
Lys Ala Lys Gly Gln Pro Arg Glu Pro Gln Val Tyr Thr Leu Pro Pro
            500                 505                 510
Ser Gln Glu Glu Met Thr Lys Asn Gln Val Ser Leu Thr Cys Leu Val
        515                 520                 525
Lys Gly Phe Tyr Pro Ser Asp Ile Ala Val Glu Trp Glu Ser Asn Gly
        530                 535                 540
Gln Pro Glu Asn Asn Tyr Lys Thr Thr Pro Pro Val Leu Asp Ser Asp
545                 550                 555                 560
Gly Ser Phe Phe Leu Tyr Ser Arg Leu Thr Val Asp Lys Ser Arg Trp
                565                 570                 575
Gln Glu Gly Asn Val Phe Ser Cys Ser Val Met His Glu Ala Leu His
            580                 585                 590
Asn His Tyr Thr Gln Lys Ser Leu Ser Leu Ser Leu Gly Lys
        595                 600                 605

<210> SEQ ID NO 13
<211> LENGTH: 1821
<212> TYPE: DNA
<213> ORGANISM: Artificial Sequence
<220> FEATURE:
<223> OTHER INFORMATION: Coding sequence of single-chain antibody fused
      with the Fc fragment

<400> SEQUENCE: 13
atggacatgc gggtccccgc tcaactgctg ggccttcttt tgctctggtt gccgggtgca      60
agatgccagg taaccctgaa agaatccgga ccggccttgg taaagccgac gcagacccctt   120 actctcacat gtacgtttag tggattctca ttgtctacat caggaacatg tgtcagctgg    180
atccggcagc cgcccggtaa agccctggag tggcttgcca caatatgttg gaggatagc     240 aaaggatact ccacaagtct taagagtcgc ctgactatta gcaaagacac gtccaagaat   300
caggccgtgc tcaccatgac caatatggac ccagtagata ctgcgaccta ctattgcgct    360
agacgggaag attcagggta cttctggttc ccttactggg acaggggac tctggttacc    420 gtgtcatctg gtggaggggg tagcggtgga ggtggaagtg gtggcggagg aagtggcgga    480
ggtgggtccg gaggcggcgg ctccggagga ggtggttcag atattcagat gacacagagc   540
ccttcttcac ttagtgcctc agtaggggac cgcgtcacta tcacatgccg ggccgggcag   600
aacgtgcaga actacttggc ttggtatcag cagaagcccg gaaaagcgcc caaagtgctg   660
```

-continued

```
atcttcaacg ctcagtcact gcagactgga gtgccttcca ggttttctgg tagcggctct    720
gggaccgatt tcacactcac aatctcttct ctgcagccag aggacttcgc cacttactac    780
tgccaacagt acaattcctg cctactttt ggtggaggga caaaggtaga gattaaagca    840
agtaccaaag gaccatctgt cttccctctg caccatgca gccggagcac cagcgagtct    900
accgctgcgc tcggctgcct tgtgaaggac tacttcccag aacctgtgac tgtgtcatgg    960
aatagcggcg ctctgaccag tggagttcac accttccccg ctgtcctgca gagcagcgga   1020
ttgtactctc tctccagcgt ggtgaccgtg cccagttcct ccctcggtac taagacgtat   1080
acatgcaatg tggaccacaa gccctccaat accaaggtcg acaagcgggt agaatcaaaa   1140
tatgggccgc cttgtccccc ctgccctgct cctgagtttc tcggagggcc cagcgtcttc   1200
ctctttccac ctaagccaaa agatacactg atgatctccc ggaccccgga ggtgacatgt   1260
gtggtggtgg atgtgtccca ggaggatcct gaggtgcagt ttaactggta cgtcgacgga   1320
gtcgaagtac acaacgccaa gacgaagccc gagaggaac agtttaatag tacctataga   1380
gtcgtcagtg tgttgaccgt tcttcatcag gattggctga atgggaaaga atataaatgc   1440
aaggtttcca ataaaggact cccatcctca atcgagaaaa ccattagcaa agccaaagga   1500
cagccaagag agccccaagt ctacacgctg ccccttcac aggaagagat gaccaaaaac   1560
caggtttccc ttacctgctt ggtgaagggc ttttaccct cagatatcgc ggtggagtgg   1620
gagagcaatg ggcagcccga gaataattac aaaacaacgc cgccagtgct tgattcagac   1680
ggctcatttt tcctgtactc tcgactgact gtggacaaaa gcaggtggca ggaggggaat   1740
gttttctctt gttctgtgat gcatgaggct ctccacaacc actacacaca aaagtcactg   1800
tccttgagcc tcggcaagta a                                              1821
```

<210> SEQ ID NO 14
<211> LENGTH: 22
<212> TYPE: PRT
<213> ORGANISM: Artificial Sequence
<220> FEATURE:
<223> OTHER INFORMATION: Signal peptide

<400> SEQUENCE: 14

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 15
<211> LENGTH: 30
<212> TYPE: PRT
<213> ORGANISM: Artificial Sequence
<220> FEATURE:
<223> OTHER INFORMATION: Linker peptide

<400> SEQUENCE: 15

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 16
<211> LENGTH: 22
<212> TYPE: PRT
<213> ORGANISM: Artificial Sequence
<220> FEATURE:

<223> OTHER INFORMATION: Signal peptide

<400> SEQUENCE: 16

Met Asp Met Arg Val Pro Ala Gln Leu Leu Gly Leu Leu Leu Leu Trp
1               5                   10                  15
Phe Pro Gly Ser Arg Cys
            20

<210> SEQ ID NO 17
<211> LENGTH: 11
<212> TYPE: PRT
<213> ORGANISM: Artificial Sequence
<220> FEATURE:
<223> OTHER INFORMATION: CDR1 of light chain variable region

<400> SEQUENCE: 17

Arg Ala Gly Gln Asn Val Gln Asn Tyr Leu Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: CDR2 of light chain variable region

<400> SEQUENCE: 18

Asn Ala Gln Ser Leu Gln Thr
1               5

<210> SEQ ID NO 19
<211> LENGTH: 8
<212> TYPE: PRT
<213> ORGANISM: Artificial Sequence
<220> FEATURE:
<223> OTHER INFORMATION: CDR3 of light chain variable region

<400> SEQUENCE: 19

Gln Gln Tyr Asn Ser Trp Pro Thr
1               5

<210> SEQ ID NO 20
<211> LENGTH: 9
<212> TYPE: PRT
<213> ORGANISM: Artificial Sequence
<220> FEATURE:
<223> OTHER INFORMATION: CDR1 of heavy chain variable region

<400> SEQUENCE: 20

Gly Phe Ser Leu Ser Thr Ser Gly Thr
1               5

<210> SEQ ID NO 21
<211> LENGTH: 5
<212> TYPE: PRT
<213> ORGANISM: Artificial Sequence
<220> FEATURE:
<223> OTHER INFORMATION: CDR2 of heavy chain variable region

<400> SEQUENCE: 21

Cys Trp Glu Asp Ser
1               5

<210> SEQ ID NO 22
<211> LENGTH: 10
<212> TYPE: PRT

```
<213> ORGANISM: Artificial Sequence
<220> FEATURE:
<223> OTHER INFORMATION: CDR3 of heavy chain variable region

<400> SEQUENCE: 22

Glu Asp Ser Gly Tyr Phe Trp Phe Pro Tyr
1               5                   10
```

ONCOLYTIC VIRUS EXPRESSING PD-1 BINDING PROTEIN AND APPLICATION OF ONCOLYTIC VIRUS

CROSS REFERENCE TO RELATED APPLICATIONS

This application is a US National Phase application based upon PCT Application No. PCT/CN2019/112905 filed Oct. 24, 2019, which claims the priority of Chinese Patent Application No. 201811259785.9, filed on Oct. 26, 2018, and titled with "ONCOLYTIC VIRUS EXPRESSING PD-1 BINDING PROTEIN AND APPLICATION OF ONCOLYTIC VIRUS", and the disclosures of which are hereby incorporated by reference in its entirety.

FIELD

The present disclosure relates to the technical field of tumor therapy using an oncolytic virus, specifically to an oncolytic adenovirus expressing PD-1 binding protein, methods for preparing the same and uses thereof.

BACKGROUND

According to statistics, more than 12 million people worldwide are diagnosed with cancer per year, and cancer has a serious impact on the health and development of human beings. Affected by medical and environmental conditions, the cancer mortality rate in China is higher than the global average. Traditional tumor therapy has disadvantages such as poor efficacy, high mortality, and high prognostic recurrence rate, so it poses a major challenge to the treatment of cancer. For example, in the very early stage of tumor development, micrometastasis has already occurred and is located in tissues far away from the original site of the tumor. Therefore, when diagnosed with cancer, many patients have already experienced micrometastasis.

Tumor-reactive T cells can find and disrupt these micrometastases, and allow the surrounding healthy tissue to be preserved. However, the naturally occurring T cells in response to malignant tumors are usually not sufficient to effectively inhibit the regression of primary or metastatic tumors. Novel therapies, such as immunotherapy including PD-1 antibodies, PD-L1 antibodies and the popular CAR-T technology in recent years, aim to enhance the patient's immune response to tumors in order to eliminate primary or metastatic tumor cells. In addition, as another promising therapy, oncolytic viruses can replicate within tumor cells and break the cells, thereby continuously killing tumor cells. Moreover, the oncolytic virus can also carry antioncogenes, etc. to exert the ability of antioncogenes to kill tumor cells while using the virus to break cells, thereby improving the therapeutic effect.

There is still an urgent need for new manners to enhance the efficacy of oncolytic viruses, thereby increasing the chance of clinical success.

SUMMARY

In the present disclosure, the structure of the oncolytic adenovirus is modified by replacing the E1A wild-type promoter in viral genome with a survivin promoter, which allows the modified oncolytic adenovirus replicating only in tumor cells with survivin promoter activity but not in normal cells, enhancing the targeting of the oncolytic adenovirus to tumor cells. Also, the E1B gene is inactivated, which allows the adenovirus preferentially replicating in cancer cells without normal p53 function. Further, the PD-1 binding protein coding sequence is introduced into viral genome, which allows the oncolytic virus not only has oncolytic properties but additionally immunomodulatory effect by inhibiting PD-1. More importantly, the inventors unexpectedly found that the structure of the PD-1 binding protein has a crucial impact on the therapeutic effect of the oncolytic virus. Introducing a specific form of PD-1 single-chain antibody linked to an immunoglobulin Fc fragment on the C-terminus can bring unexpected improvement to the anti-tumor effect of the oncolytic virus in vivo and in vitro. Based on the above findings, the inventor completed this invention.

Specifically, the first aspect of the present disclosure provides an oncolytic virus comprising a nucleic acid encoding a PD-1 binding protein capable of inhibiting PD-1 activity.

In one embodiment, the virus is an adenovirus.

In another embodiment, the promoter of the virus is replaced by a survivin promoter.

In another embodiment, the activity of E1B gene is reduced or completely inactivated, preferably, the E1B gene is knocked out from the viral genome.

In another embodiment, the PD-1 binding protein is a fusion polypeptide comprising a PD-1 single-chain antibody and an immunoglobulin Fc fragment.

In another embodiment, the fusion polypeptide has a structure of $S\text{-}V_L\text{-}L\text{-}V_H\text{-}Fc$;

wherein S is an optional signal peptide sequence, and preferably, the signal peptide sequence is MDMRVPAQLLGLLLLWLPGARC (SEQ ID NO: 14), or MDMRVPAQLLGLLLLWFPGSRC (SEQ ID NO: 16);

$V_L$ is the light chain variable region of the PD-1 single-chain antibody, preferably comprising CDR1 with sequence RAGQNVQNYLA (SEQ ID NO: 17), CDR2 with sequence NAQSLQT (SEQ ID NO: 18) and CDR3 with sequence QQYNSWPT (SEQ ID NO: 19), and more preferably, the amino acid sequence of the light chain variable region is shown in SEQ ID NO: 4;

L is a linker, such as a flexible linker comprising or mainly consisting of Ala (A), Thr (T), Gly (G) and/or Ser (S), specifically, for example, a flexible linker comprising or mainly consisting of Gly and Ser, and for example, the linker may be 1-50 amino acids in length, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids in length, and preferably, L is $(Gly_4Ser)_m$, wherein m is a natural number between 1 and 10, such as 1, 2, 3, 4, 5, 6, 7, 8, 9 or 10, and more preferably, L is $(Gly_4Ser)_6$, or L is $A(EAAAK)_nA$, wherein n is a natural number between 1 and 9, such as 1, 2, 3, 4, 5, 6, 7, 8 or 9;

$V_H$ is the heavy chain variable region of the PD-1 single-chain antibody, preferably comprising CDR1 with sequence GFSLSTSGT (SEQ ID NO: 20), CDR2 with sequence CWEDS (SEQ ID NO: 21) and CDR3 with sequence EDSGYFWFPY (SEQ ID NO: 22), and more preferably, the amino acid sequence of the heavy chain variable region is shown in SEQ ID NO: 3; and Fc is an immunoglobulin Fc fragment, wherein the Fc fragment can be derived from human immunoglobulin, and the Fc fragment can be derived from the Fc fragment of IgG, IgA, IgD, IgE or IgM, and preferably, the Fc fragment is derived from the Fc fragment of IgG, such as from the Fc fragment of IgG1, IgG2, IgG3 or IgG4, and more preferably, the Fc fragment is derived from IgG4, and wherein the Fc fragment may have one or more amino acid substitutions, additions and/or deletions compared with its source sequence, and preferably the sequence of the Fc fragment is shown in SEQ ID NO:9.

In another embodiment, the nucleic acid sequence is operably linked to a promoter; preferably, the promoter is a CMV promoter.

In another embodiment, the oncolytic virus named Recombinant Human Type 5 Adenovirus Ad-sp-E1A-ΔE1B-anti-PD1-3 was deposited at China Center for Type Culture Collection (CCTCC, Address: 299 Bayi Road, Wuchang District, Wuhan City, Hubei Province, P.R. China, Post Code: 430072) on Aug. 21, 2018, under the accession number CCTCC NO: V201853.

The second aspect of the present disclosure provides use of the oncolytic virus of the first aspect in the manufacture of a medicament for the treatment of a proliferative disease, and preferably, the proliferative disease is a tumor, such as prostate cancer, breast cancer, colorectal cancer, lung cancer, liver cancer, melanoma, head and neck cancer, lymphoma, gastric cancer, esophageal cancer, ovarian cancer, head and neck squamous cell carcinoma, bladder cancer, or kidney cancer.

The third aspect of the present disclosure provides a pharmaceutical composition comprising the oncolytic virus of the first aspect, and optionally a pharmaceutically acceptable carrier.

In one embodiment, the pharmaceutical composition is formulated for oral, nebulized inhalation, intravenous, intramuscular, subcutaneous, perfusion, intralesional injection, or intratumoral administration.

In a specific embodiment, the pharmaceutical composition comprises the oncolytic virus in an amount of about $10^8$ viral particles (vp) to $10^{12}$ vp (e.g., $1.5 \times 10^{10}$ vp)

The fourth aspect of the present disclosure provides a method of treating a proliferative disease, comprising administering the oncolytic virus in the first aspect or the pharmaceutical composition in the third aspect to a subject in need thereof, and preferably, the proliferative disease is a tumor, such as prostate cancer, breast cancer, colorectal cancer, lung cancer, liver cancer, melanoma, head and neck cancer, lymphoma, gastric cancer, esophageal cancer, ovarian cancer, head and neck squamous cell carcinoma, bladder cancer, or kidney cancer.

In one embodiment, the oncolytic virus is administered to the subject in an amount of about $10^8$ vp to $10^{12}$ vp (e.g., $1.5 \times 10^{10}$ vp) by oral, nebulized inhalation, intravenous, intramuscular, subcutaneous, perfusion, intralesional injection, or intratumoral administration, with an administration number of 1-6 (for example, 1, 2, 3, 4, 5, or 6), and an administration interval of every 1, 2, 3, 4, 5, 6, 7 or more days, or 1, 2, 3, 4, 5, 6 or more times over the course of one day.

The oncolytic virus provided by the present disclosure has good safety, as well as inhibitory effect on tumors in vivo and in vitro, which is significantly superior to the existing clinical drugs sorafenib and gemcitabine, and therefore has broad clinical application prospects.

DETAILED DESCRIPTION

Figure 1:
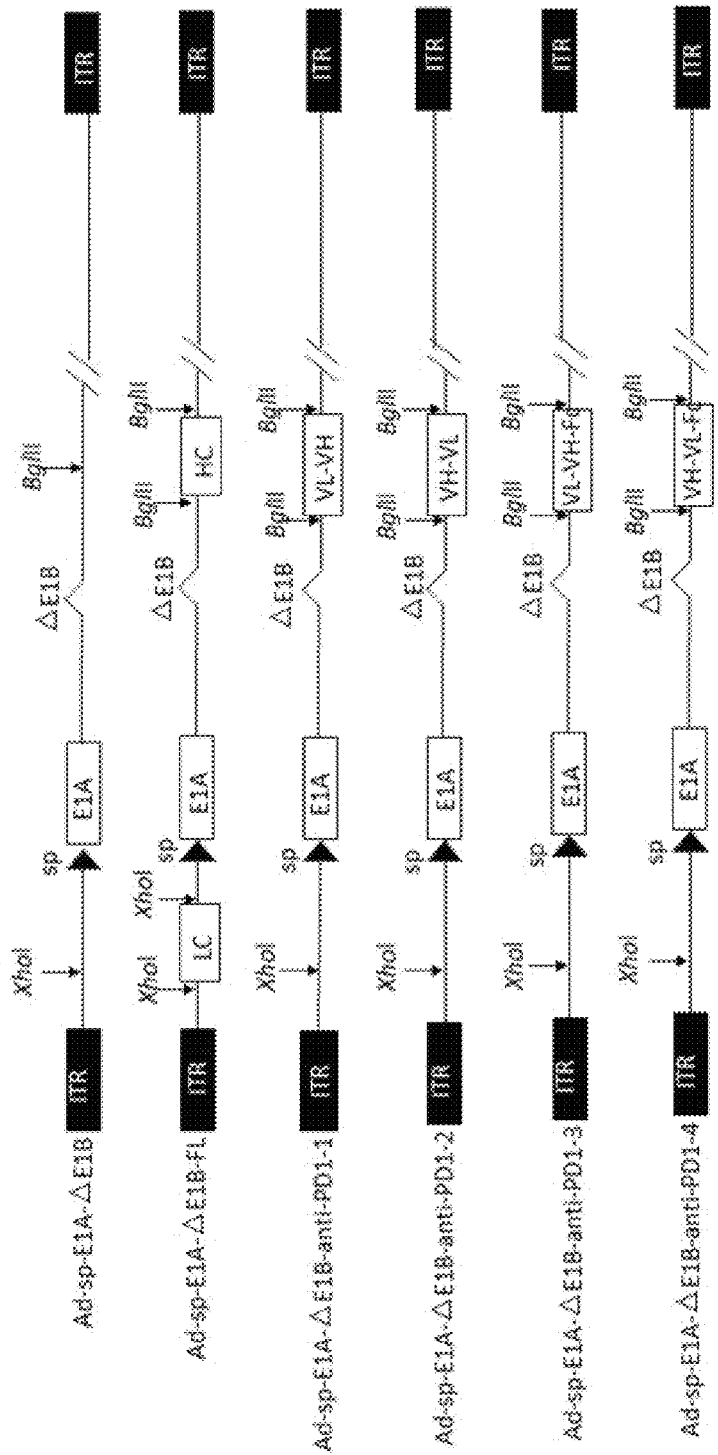
FIG. 1 is a schematic diagram for construction of recombinant oncolytic adenovirus Ad-sp-E1A-ΔE1B-anti-PD1 with different antibody structures and sequences.

The term used in this application has the same meaning as in the prior art. In order to clearly indicate the meaning of the terms used, the specific meanings of some terms in this application are given below. When the definition herein conflicts with the conventional meaning of the term, the definition herein shall prevail.

Definitions

The term "oncolytic virus" refers to a virus capable of selectively replicating in tumor cells or hyperproliferative cells thereby slowing the cell growth or inducing the cell, while having no or minimal effect on normal cells. Exemplary oncolytic viruses include vesicular stomatitis virus (VSV), Newcastle disease virus (NDV), herpes simplex virus (HSV), reovirus, measles virus, retrovirus, influenza virus, Sinbis virus, vaccinia virus, and adenovirus (Kim et al., Nat. Med. 7:781 (2001); Coffey et al., Science 282: 1332 (1998); Lorence et al., Cancer Res. 54: 6017 (1994); and Peng et al., Blood 98: 2002 (2001)).

The term "PD-1", or programmed cell death protein 1, is an important immunosuppressive molecule. Immunoregulation targeting PD-1 is of great significance for anti-tumor, anti-infection, anti-autoimmune diseases, and organ transplant survival. The endogenous ligand of PD-1 is PD-L1 (programmed cell death 1 ligand 1), which is a member of the B7 family and is expressed on the surface of most tumor cells, such as gastric cancer, lung cancer, breast cancer, cervical cancer, intestinal cancer, melanoma, liver cancer, ovarian cancer, kidney cancer, pancreatic cancer, glioma and leukemia. PD-L1 is also an important immunosuppressive molecule. By binding to PD-L1, PD-1 inhibits the proliferation of T cells thereby suppressing the immune response.

The binding of PD-L1 to PD-1 on the surface of activated T cells promotes the phosphorylation of SHP-1 and inhibits the phosphorylation of CD3δ and Zap-70, thereby blocking TCR signaling. In addition, PD-1/PDL1 signal can also inhibit the activity of PI3K and Akt and then block CD28 signal, which leads to the inhibition of T cells functions such as cytokines secretion, proliferation and killing, causing the eventual elimination of T cells after their apoptosis and necrosis. The PD-1/PD-L1 interaction not only blocks the first and second signals of T cell activation, but also inhibits the activation and proliferation of effector T cells, and furthermore, regulatory T cells exert stronger immune suppression and even induce the transformation of Th cells into Treg cells. Currently, a large number of studies have shown that blocking PD-1/PD-L1 signal can effectively increase the number of effector T cells and reduce the number of Treg cells, and inhibits tumor growth and metastasis, therefore greatly extending the survival time of tumor-bearing mice. For those patients with advanced cancer, when they are not suitable for surgery, chemotherapy and radiotherapy, immunotherapy is currently the most effective method. At present, there are abundant inhibitory antibodies against blocking PD-1/PD-L1 signals, and the treatment of melanoma with these antibodies has achieved good outcomes and effectively prolonged the patient's survival period. The "PD-1 activity" or "PD-1 function" mentioned herein refers to the aforementioned physiological effects or functions of the PD-1 protein in the in vivo or in vitro system.

The term "PD-1 binding protein" refers to a protein capable of binding to PD-1 protein and inhibiting the function of PD-1 protein.

The "inhibition" or "suppression" used herein means that the activity or function of the target protein, such as PD-1, is partially reduced or completely lost. Those skilled in the art know how to measure the degree of reduction in the function or activity of a protein.

Survivin, a member of the inhibitor of apoptosis (IAP) family, is specifically and highly expressed in most malignant tumors. The promoter of survivin gene has strong transcriptional activity in tumor cells, and mediates the specific expression of target genes in various tumor cells, but not in normal differentiated cells and resting vascular endothelial cells, so it has a high specificity to tumor tissue. The term "survivin promoter" refers to the promoter region sequence of survivin gene. The survivin promoter can be derived from any source of animals, preferably mammals, such as human. Besides, the survivin promoter may also comprise one or more additions, deletions and/or substitutions in base sequence, as long as the survivin promoter still maintains the expression specificity.

The term "single-chain antibody", namely single-chain antibody fragment, scFv, refers to an antibody formed by linking a heavy chain variable region and a light chain variable region of an antibody through a linker. The linker is a flexible peptide comprising or mainly consisting of A, T, G and/or S, and in one embodiment is a flexible peptide consisting of G and S. The linker may be 1-50 or more amino acids in length, for example, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 50 amino acids in length.

In one embodiment, the linker is selected from the following sequences: $(Gly_4Ser)$, $(Gly_4Ser)_2$, $(Gly_4Ser)_3$, $(Gly_4Ser)_4$, $(Gly_4Ser)_5$, $(Gly_4Ser)_6$, $(Gly_4Ser)_7$, $(Gly_4Ser)_8$, $(Gly_4Ser)_9$, and $(Gly_4Ser)_{10}$. In a preferred embodiment, the linker is $(Gly_4Ser)_6$ (SEQ ID NO: 15).

In another embodiment, the linker is selected from the following sequences: $A(EAAAK)_2A$, $A(EAAAK)_3A$, $A(EAAAK)_4A$, $A(EAAAK)_5A$, $A(EAAAK)_6A$, $A(EAAAK)_7A$, $A(EAAAK)_8A$, and $A(EAAAK)_9A$.

The term "immunoglobulin Fc fragment" or "Fc fragment of immunoglobulin" refers to a protein fragment comprising the heavy chain constant region 1 (CH1), heavy chain constant region 2 (CH2) and heavy chain constant region 3 (CH3) of immunoglobulin, but not comprising heavy chain and light chain variable regions of immunoglobulin. It may also comprise the hinge region located in the heavy chain constant region.

Furthermore, the immunoglobulin Fc fragment of the present disclosure may comprise part or all of the Fc fragment comprising the heavy chain constant region 1 (CH1) and/or the light chain constant region (CL) apart from the heavy chain and light chain variable regions, as long as it has a physiological function that is basically similar to or better than that of natural protein. Besides, it may be a fragment obtained by a deletion in the relatively long part of the CH2 and/or CH3 amino acid sequences. For example, the immunoglobulin Fc fragment of the present disclosure may comprise: 1) CH1 domain, CH2 domain and CH3 domain; 2) CH1 domain and CH2 domain; 3) CH1 domain and CH3 domain; 4) CH2 domain and CH3 domain; 5) CH1 domain, CH2 domain, CH3 or CL domain; 6) a combination of one or more constant region domains and (part or all of) hinge region of immunoglobulin; or 7) a dimer of any two domains of the heavy chain and light chain constant regions. In a word, the immunoglobulin Fc fragment of the present disclosure means having one or more heavy chain/light chain constant region domains or variant forms thereof, such as single-chain Fc and monomer Fc.

In addition, the immunoglobulin Fc fragment of the present disclosure may comprise natural amino acid sequences and sequence variants (mutants) thereof. Due to one or more deletions, additions, non-conservative or conservative substitutions or combinations thereof of amino acid residues, the amino acid sequence derivative has a sequence different from the natural amino acid sequence. For example, in IgG Fc fragment, amino acid residues at positions 214 to 238, 297 to 299, 318 to 322, or 327 to 331 that are known to be critical for binding can be used as suitable positions for modification. Besides, the immunoglobulin Fc fragment of the present disclosure can also comprise a variety of other derivatives, including those having deleted the region capable of forming disulfide bonds, those having deleted several amino acid residues at the N-terminal of the natural Fc form, or those having added methionine residues to the N-terminal of the natural Fc form.

The amino acid substitutions in proteins and peptides that do not generally change molecular activity are known in the art (H. Neurath, RL Hill, The Proteins, Academic Press, New York, 1979). The most common substitutions are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, and both directions are available.

The aforementioned Fc derivatives are derivatives that have the same biological activity as the Fc fragment or have improved structural stability (such as structural stability to heat, pH, etc.).

In addition, these Fc fragment can be derived from natural forms isolated from human and other animals including cattle, goat, pig, mouse, rabbit, hamster, rat and guinea pig, or can be derived from recombinant or derivative of transformed animal cells or microorganisms. Herein, the Fc fragment can be obtained from natural immunoglobulin by separating intact immunoglobulin from human or animal organisms and treating them with proteolytic enzymes. Papain digests natural immunoglobulin into Fab and Fc fragments, while pepsin treatment results in the production of pFc' and $F(ab')_2$ fragments. Fc or pFc' can be isolated from these fragments by, for example, size exclusion chromatography.

In addition, the immunoglobulin Fc fragment may be an Fc fragment derived from IgG, IgA, IgD, IgE, and IgM, or prepared by a combination or hybrid thereof. Preferably, it is derived from IgG or IgM (two of the most abundant proteins in human blood), most preferably from IgG (which is known to extend the half-life of ligand-binding protein).

Additionally, it should also be noted that, as used in this specification, the singular form includes the plural form of the object to which it refers, unless it is clearly and explicitly limited to one object. If a specific numerical value is mentioned, at least that value will be included, unless the context clearly indicates that it refers otherwise.

When a numerical value represents an approximate value, it should be understood that the specific numerical value forms another embodiment. As used herein, "about X" (where X is a number) means±10% (inclusive) of the listed value. If present, all ranges are inclusive and combinable.

Terms such as "comprising", "including", and "containing" as used herein are not intended to be limiting. In addition, unless otherwise indicated, "or" means "and/or".

The term "pharmaceutical composition" as used herein means a combination of at least one drug and optionally a pharmaceutically acceptable carrier or excipient that are combined together to achieve a particular purpose. In certain embodiments, the pharmaceutical composition includes combinations that are separated in time and/or space as long as they can work together to achieve the purpose of the present disclosure. For example, the components of the pharmaceutical composition may be administered to the subject as a whole or separately. When the ingredients contained in the pharmaceutical composition are separately administered to a subject, the ingredients may be administered to the subject simultaneously or sequentially. Preferably, the pharmaceutically acceptable carrier is water, a buffered aqueous solution, an isotonic saline solution such as PBS (phosphate buffered saline), glucose, mannitol, dextrose, lactose, starch, magnesium stearate, cellulose, magnesium carbonate, 0.3% glycerol, hyaluronic acid, or polyalkylene glycols such as polypropylene glycol, triglycerides and the like. The type of the pharmaceutically acceptable carrier used depends in particular on whether the composition according to the present disclosure is formulated for oral, nasal, intratumoral, perfusion, intradermal, subcutaneous, intramuscular, intralesional or intravenous administration.

The composition according to the present disclosure may contain a lubricant, a preservative, a stabilizer, a wetting agent, an emulsifier, salts that affect osmotic pressure, a buffer, coloring substances, flavoring substances and/or aromatic substances, etc., as an additive.

"Administration" or "administering" means to provide a substance, such as a pharmaceutical composition, to a subject in a pharmacologically acceptable manner.

The dosage of a pharmaceutical composition provided to a subject refers to a dose sufficient to show its benefit to the administered subject, and may also be referred to herein as a "pharmaceutical effective amount" or "effective amount". The actual amount administered, as well as the rate and time-course of administration, will depend on the condition and severity of the subject being treated. Prescription of treatment, e.g., decisions on dosage, etc., is ultimately within the responsibility of general practitioners and other medical doctors and relies on decisions of them, and typically takes account of the disease being treated, the condition of the individual patient, the site of delivery, the method of administration, and other factors known to physicians.

In an embodiment of the present disclosure, the pharmaceutical composition comprises the oncolytic virus in an amount of $10^8$ vp to $10^{12}$ vp, such as $1\times10^8$, $1.5\times10^8$, $2\times10^8$, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $1.5\times10^9$, $2\times10^9$, $2.5\times10^9$, $3\times10^9$, $3.5\times10^9$, $4\times10^9$, $4.5\times10^9$, $5\times10^9$, $5.5\times10^9$, $6\times10^9$, $6.5\times10^9$, $7\times10^9$, $7.5\times10^9$, $8\times10^9$, $8.5\times10^9$, $9\times10^9$, $9.5\times10^9$, $1\times10^{10}$, $1.5\times10^{10}$, $2\times10^{10}$, $2.5\times10^{10}$, $3\times10^{10}$, $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$ or $1\times10^{12}$ vp, and any dosage between the above two.

In another embodiment, a single dose of the oncolytic virus administered to the subject is in an amount of $10^8$ vp to $10^{12}$ vp, such as $1\times10^8$, $1.5\times10^8$, $2\times10^8$, $2.5\times10^8$, $3\times10^8$, $3.5\times10^8$, $4\times10^8$, $4.5\times10^8$, $5\times10^8$, $5.5\times10^8$, $6\times10^8$, $6.5\times10^8$, $7\times10^8$, $7.5\times10^8$, $8\times10^8$, $8.5\times10^8$, $9\times10^8$, $9.5\times10^8$, $1\times10^9$, $1.5\times10^9$, $2\times10^9$, $2.5\times10^9$, $3\times10^9$, $3.5\times10^9$, $4\times10^9$, $4.5\times10^9$, $5\times10^9$, $5.5\times10^9$, $6\times10^9$, $6.5\times10^9$, $7\times10^9$, $7.5\times10^9$, $8\times10^9$, $8.5\times10^9$, $9\times10^9$, $9.5\times10^9$, $1\times10^{10}$, $1.5\times10^{10}$, $2\times10^{10}$, $2.5\times10^{10}$, $3\times10^{10}$, $3.5\times10^{10}$, $4\times10^{10}$, $4.5\times10^{10}$, $5\times10^{10}$, $5.5\times10^{10}$, $6\times10^{10}$, $6.5\times10^{10}$, $7\times10^{10}$, $7.5\times10^{10}$, $8\times10^{10}$, $8.5\times10^{10}$, $9\times10^{10}$, $9.5\times10^{10}$, $1\times10^{11}$, $1.5\times10^{11}$, $2\times10^{11}$, $2.5\times10^{11}$, $3\times10^{11}$, $3.5\times10^{11}$, $4\times10^{11}$, $4.5\times10^{11}$, $5\times10^{11}$, $5.5\times10^{11}$, $6\times10^{11}$, $6.5\times10^{11}$, $7\times10^{11}$, $7.5\times10^{11}$, $8\times10^{11}$, $8.5\times10^{11}$, $9\times10^{11}$, $9.5\times10^{11}$ or $1\times10^{12}$ vp, and any dosage between the above two. The administration number per course of treatment is 1-6, for example, 1, 2, 3, 4, 5 or 6, and the administration interval can be every 1, 2, 3, 4, 5, 6, 7 or more days, or 1, 2, 3, 4, 5, 6 or more times over the course of one day.

In the present disclosure, the unit of virus dose is vp (viral particle), which represents the number of virus particles contained in the virus solution, and is virus particle titer.

The term "subject" as used herein means animals, including warm-blooded mammals such as human and primate; birds; domesticated domestic or farm animals such as cats, dogs, sheep, goats, cattle, horses and pigs; laboratory animals such as mice, rats and guinea pigs; fish; reptiles; zoo animals and wild animals, etc.

Unless defined otherwise, all technical and scientific terms used herein have the same meaning as commonly understood by those skilled in the art.

Unless otherwise specified, any component, element, attribute or step disclosed in an embodiment of the method and product can be applied to any other method and product disclosed herein.

Each patent, patent application, cited publication, or description in this this disclosure is incorporated herein by reference in its entirety.

The present disclosure is further illustrated by the following examples. It should be understood that these examples are provided for illustration only and are not intended to limit the scope of the present disclosure. From the above discussion and these examples, those skilled in the art can determine the essential characteristics of the present disclosure, and make various changes and modifications to the present disclosure to adapt it to various usages and conditions without departing from the spirit and scope of the present disclosure

EXAMPLES

Materials and Methods

Synthesis of pCA13-Anti-PD1

The anti-PD1 gene expression cassette fragments with EcoRI restriction site at the 5' end and XbaI restriction site at the 3' end were synthesized (4 fragments in total, and the sequence of each anti-PD1 gene expression cassette is shown in SEQ ID. NO: 6, 8, 11 or 13 (the sequences of expression cassette fragments do not contain restriction sites)) (Union-Biotech (Shanghai) Co., Ltd.) and then subjected to double restriction digestion with EcoRI and XbaI, followed by recovering the digested fragments. The restriction digestion system is as follows:

| | |
|---|---|
| Anti-PD1 fragment | 10 μL |
| EcoRI | 0.5 μL |
| XbaI | 0.5 μL |
| 10 × Buffer | 2 μL |
| ddH$_2$O | 7 μL |
| Total | 20 μL |

The above reaction system was placed in a 37° C. water bath for 2 hours.

Meanwhile, pCA13 plasmid was subjected to double restriction digestion with EcoRI and XbaI using the above restriction digestion system, followed by recovering the digested large fragments. Then the above digested gene fragments and vector fragments were ligated using Ligation High Ligase (TOYOBO). The ligation system is as follows:

| | |
|---|---|
| Linearized pCA13 plasmid | 0.5 μL |
| Anti-PD1 fragment | 5.5 μL |
| Ligation High | 4 μL |
| Total | 10 μL |

The above reaction system was placed in a water bath at 16° C. for 2 hours, and the ligation product obtained was pCA13-anti-PD1.

Construction of pShuttle-sp-E1A-ΔE1B a. Construction of pShuttle-E1A-E1B Plasmid The pShuttle plasmid (Shanghai Jiran Biotechnology Co., Ltd.) and the adenovirus vector pXC2 plasmid (a gift from Academician Liu Xinyuan, Shanghai Institute of Biochemistry and Cell Biology, Shanghai Institutes for Biological Sciences, Chinese Academy of Sciences) were subjected to double restriction digestion with XhoI and MfeI, and the restriction digestion systems are as follows:

Double Restriction Digestion System with XhoI and MfeI for pShuttle

| | |
|---|---|
| pShuttle | 10 μL |
| XhoI | 0.5 μL |
| MfeI | 0.5 μL |
| 10 × Buffer | 2 μL |
| ddH$_2$O | 7 μL |
| Total | 20 μL |

Double Restriction Digestion System with XhoI and MfeI for pXC2

| | |
|---|---|
| pXC2 | 10 μL |
| XhoI | 0.5 μL |
| MfeI | 0.5 μL |
| 10 × Buffer | 2 μL |
| ddH$_2$O | 7 μL |
| Total | 20 μL |

The above reaction system was placed in a 37° C. water bath for 2 h, and then subjected to agarose gel electrophoresis to recover the large fragment digested from pShuttle plasmid and the small fragment digested from pXC2 plasmid. Then the above recovered products were ligated using ligase to construct pShuttle-E1A-E1B plasmid, and the ligation system is as follows:

| | |
|---|---|
| Linearized pShuttle plasmid | 4 μL |
| Linearized pXC2 plasmid | 2 μL |
| Ligation High | 4 μL |
| Total | 10 μL |

The above reaction system was placed in a water bath at 16° C. for 2 hours, and the ligation product obtained was pShuttle-E1A-E1B.

b. Construction of pShuttle-E1A-ΔE1B Plasmid

The E1B region in pShuttle-E1A-E1B plasmid was deleted by Overlap PCR to obtain pShuttle-E1A-ΔE1B plasmid. The specific amplification primers designed are as follows:

```
XhoI-F1:
GCCTCGAGGTCGACTACGTA

ΔE1B-R1:
TCAGCACCTTCCAGATCTGAGGTCAGATGTAACCAAGATTA

ΔE1B-F1:
TCTTGGTTACATCTGACCTCAGATCTGGAAGGTGCTGAGGT

MfeI-R1:
TCCAATTGTGCCAAAAGAGCCGT.
```

Overlap PCR

The PCR reaction system 1 is as follows:

| | |
|---|---|
| pShuttle-E1A-E1B | 2 μL |
| XhoI-F1 | 1.5 μL |
| ΔE1B-R1 | 1.5 μL |
| KOD enzyme | 1 μL |
| 2 mM dNTPs | 5 μL |
| 25 mM MgSO$_4$ | 3 μL |
| 10 × Buffer | 5 μL |
| ddH$_2$O | 31 μL |
| Total | 50 μL |

The PCR reaction system 2 is as follows:

| | |
|---|---|
| pShuttle-E1A-E1B | 2 μL |
| ΔE1B-F1 | 1.5 μL |
| MfeI-R1 | 1.5 μL |
| KOD enzyme | 1 μL |
| 2 mM dNTPs | 5 μL |
| 25 mM MgSO$_4$ | 3 μL |
| 10 × Buffer | 5 μL |
| ddH$_2$O | 31 μL |
| Total | 50 μL |

The PCR reaction program is as follows:

| | | |
|---|---|---|
| 98° C. pre-denaturation | 2 min | |
| 98° C. denaturation | 10 sec | |
| 55° C. annealing | 30 sec | 30 cycles |
| 68° C. extension | 1 min | |
| 68° C. extension | 5 min | |

The obtained reaction products were stored at 4° C.

The above reaction products were subjected to 1% agarose gel electrophoresis to recover the target band 1 and target band 2 respectively. Then, the target bands 1 and 2 were spliced together through the following PCR reaction process. The PCR reaction system is as follows:

| | |
|---|---|
| Target band 1 | 2 μL |
| Target band 2 | 2 μL |
| KOD enzyme | 1 μL |
| 2 mM dNTPs | 5 μL |
| 25 mM MgSO$_4$ | 3 μL |
| 10 × Buffer | 5 μL |
| ddH$_2$O | 31 μL |
| Total | 49 μL |

After 8 cycles of PCR, primers XhoI-F1 and MfeI-R1 were added, 1.5 μL of each primer, and then the PCR reaction was continued as follows:

| | | |
|---|---|---|
| 98° C. pre-denaturation | 2 min | |
| 98° C. denaturation | 10 sec | |
| 55° C. annealing | 30 sec | 8 cycles + 25 cycles |
| 68° C. extension | 1 min | |
| 68° C. extension | 5 min | |

The obtained reaction products were stored at 4° C.

The above reaction products were subjected to 1% agarose gel electrophoresis to recover the target band 3. Then the recovered target band 3 was subjected to double restriction digestion with XhoI and MfeI, and meanwhile pShuttle-E1A-E1B plasmid was subjected to double restriction digestion with the same restriction enzymes. The restriction digestion system is as follows:

| | |
|---|---|
| Target band 3/pShuttle-E1A-E1B | 10 μL |
| XhoI | 0.5 μL |
| MfeI | 0.5 μL |
| 10 × Buffer | 2 μL |
| ddH$_2$O | 7 μL |
| Total | 20 μL |

The above reaction system was placed in a 37° C. water bath for 2 h, and then subjected to agarose gel electrophoresis to recover the nucleic acid fragments digested from the target band 3 and the large fragments digested from pShuttle-E1A-E1B plasmid. Then the above recovered products were ligated using ligase to construct pShuttle-E1A-ΔE1B plasmid. The ligation system is as follows:

| | |
|---|---|
| Digested target band 3 | 1 μL |
| Digested pShuttle-E1A-E1B | 5 μL |
| Ligation High | 4 μL |
| Total | 10 μL |

The above reaction system was placed in a water bath at 16° C. for 2 hours, and the ligation product obtained was pShuttle-E1A-ΔE1B plasmid.

c. Construction of pShuttle-sp-E1A-ΔE1B Plasmid

Specific primers were designed and the survivin promoter was amplified by PCR using pDRIVE-Survivin plasmid (Invivogen) as a template. Then the survivin promoter was inserted into pShuttle-E1A-ΔE1B plasmid to construct pShuttle-sp-E1A-ΔE1B plasmid. The specific primers are as follows:

Survivin-F:
GCCTCGAGCGCGTTCTTTGAAAGCAGTCGA

Survivin-R:
AGTACGTATGCCGCCGCCGCCACCT.

The PCR reaction system is as follows:

| | |
|---|---|
| pDRIVE-Survivin | 1 μL |
| Survivin-F | 1 μL |
| Survivin-R | 1 μL |
| 2 × TaqMix | 12.5 μL |
| ddH$_2$O | 9.5 μL |
| Total | 25 μL |

The PCR reaction program is as follows:

| | | |
|---|---|---|
| 94° C. pre-denaturation | 5 min | |
| 94° C. denaturation | 30 sec | |
| 55° C. annealing | 30 sec | 30 cycles |
| 72° C. extension | 30 sec | |
| 72° C. extension | 5 min | |

The obtained reaction products were stored at 4° C.

The above reaction products were subjected to 1.2% agarose gel electrophoresis to recover the target band 4. Then the recovered target band 4 was subjected to double restriction digestion with XhoI and SnaBI, and meanwhile pShuttle-E1A-ΔE1B plasmid was subjected to double restriction digestion with the same restriction enzymes. The restriction digestion system is as follows:

| | |
|---|---|
| Target band 4/pShuttle-E1A-ΔE1B | 10 μL |
| XhoI | 0.5 μL |
| SnaBI | 0.5 μL |
| 10 × Buffer | 2 μL |
| ddH$_2$O | 7 μL |
| Total | 20 μL |

The above reaction system was placed in a 37° C. water bath for 2 h, and then subjected to agarose gel electrophoresis to recover the nucleic acid fragment digested from the target band 4 and the large fragment digested from pShuttle-E1A-ΔE1B. Then the above recovered products were ligated using ligase to construct pShuttle-sp-E1A-ΔE1B plasmid. The ligation system is as follows:

| | |
|---|---|
| Digested target band 4 | 1 μL |
| Digested pShuttle-E1A-ΔE1B | 5 μL |
| Ligation High | 4 μL |
| Total | 10 μL |

The above reaction system was placed in a water bath at 16° C. for 2 hours, and the ligation product obtained was pShuttle-sp-E1A-ΔE1B plasmid.

Construction of Ad-sp-E1A-ΔE1B-anti-PD1 Plasmid

Ad-sp-E1A-ΔE1B-anti-PD1 plasmid was constructed by further modification based on pShuttle-sp-E1A-ΔE1B, wherein the anti-PD1 expression cassette was inserted into the BglII site of pShuttle-sp-E1A-ΔE1B.

I. Generation of Anti-PD1 Expression Cassette Fragment by Subjecting pCA13-Anti-PD1 to Single Restriction Digestion with BglII The restriction digestion system is as follows:

| | |
|---|---|
| pCA13-anti-PD1 | 10 μL |
| BglII | 1 μL |
| 10 × Buffer | 2 μL |
| ddH$_2$O | 7 μL |
| Total | 20 μL |

The above reaction system was placed in a 37° C. water bath for 2 h, and then subjected to 1% agarose gel electrophoresis to recover and purify the digested product.

II. Single Restriction Digestion of pShuttle-sp-E1A-ΔE1B with BglII

The restriction digestion system is as follows:

| | |
|---|---|
| pShuttle-sp-E1A-ΔE1B | 10 μL |
| BglII | 1 μL |
| 10 × Buffer | 2 μL |
| ddH$_2$O | 7 μL |
| Total | 20 μL |

The above reaction system was placed in a 37° C. water bath for 2 h, and then subjected to 1% agarose gel electrophoresis to recover and purify the digested product. Finally, the purified linearized plasmid pShuttle-sp-E1A-ΔE1B was obtained.

III. Construction of pShuttle-sp-E1A-ΔE1B-anti-PD1 Plasmid

The ligation system is as follows:

| | |
|---|---|
| Linearized pShuttle-sp-E1A-ΔE1B | 0.5 μL |
| Anti-PD1 expression cassette fragment | 5.5 μL |
| Ligation High | 4 μL |
| Total | 10 μL |

The above reaction system was placed at 16° C. overnight.

IV. Screening of Recombinant Plasmids

The above ligation products were transformed into DH5a competent cells (Beijing TransGen Biotech Co., Ltd.) through conventional transformation steps, and then the cells were spread on Kana-resistant plates to culture successfully transformed colonies. Several single colonies were picked the next day, and the plasmid was extracted from the bacterial cells after culture to identify whether the construction was successful. The successfully constructed plasmid is selected as pShuttle-sp-E1A-ΔE1B-anti-PD1.

V. Identification of pShuttle-sp-E1A-ΔE1B-anti-PD1 Plasmid

The recombinant plasmid pShuttle-sp-E1A-ΔE1B-anti-PD1 was identified by single restriction digestion.

The restriction digestion identification system is as follows:

| | |
|---|---|
| pShuttle-sp-E1A-ΔE1B-anti-PD1 | 10 μL |
| BglII | 1 μL |
| 10 × Buffer | 2 μL |
| ddH$_2$O | 7 μL |
| Total | 20 μL |

After digestion at 37° C. for 30 min, the digested products were subjected to electrophoresis to identify the correct plasmid. The clones that were identified by single restriction digestion were subjected to sequencing, and positive clones with correct direction were selected.

VI. Construction of pAd-sp-E1A-ΔE1B-anti-PD1 by Homologous Recombination

A). The successfully constructed pShuttle-sp-E1A-ΔE1B-anti-PD1 was identified by single restriction digestion with PmeI, and the reaction system was as follows:

| | |
|---|---|
| pShuttle-sp-E1A-ΔE1B-anti-PD1 | 8 μL |
| PmeI | 1 μL |
| 10 × Buffer | 2 μL |
| ddH$_2$O | 9 μL |
| Total | 20 μL |

The above reaction system was placed in a 37° C. water bath for 2 h, and then subjected to dephosphorylation experiment in the next step.

B). The linearized pShuttle-sp-E1A-ΔE1B-anti-PD1 was dephosphorylated, and the reaction system was as follows:

| | |
|---|---|
| Linearized p Shuttl e-sp-E1A-ΔE1B- anti-PD1 | 8 μL |
| FastAp (Thermo Fisher) | 1 μL |
| 10 × Buffer | 2 μL |
| ddH$_2$O | 9 μL |
| Total | 20 μL |

The above reaction system was placed in a 37° C. water bath for 30 min, and then subjected to transformation in the next step.

C). The adenovirus backbone plasmid was recombined with pShuttle-sp-E1A-ΔE1B-anti-PD1 in BJ5183 competent cells to generate pAd-sp-E1A-ΔE1B-anti-PD1. The specific steps were as follows:

(1) The linearized pShuttle-sp-E1A-ΔE1B-anti-PD1 in the previous step was transformed into BJ5183 competent cells (Reference could be made to Chinese patent application No. CN201810651914.2), and then the cells were spread on the plate. Afterward, several single colonies were picked, and cultured overnight with shaking.

(2) The plasmids were extracted from the cultured bacterial cells using a small amount of plasmid extraction kit.

D). The successfully recombined pAd-sp-E1A-ΔE1B-anti-PD1 plasmid was identified by restriction digestion, and then transformed into DH5α for a large scale of amplification.

The restriction digestion system is as follows:

| | |
|---|---|
| pAd-sp-E1A-ΔE1B-anti-PD1 | 8 μL |
| MluI | 1 μL |
| 10 × Buffer | 2 μL |
| ddH$_2$O | 9 μL |
| Total | 20 μL |

The above reaction system was placed in a 37° C. water bath for 30 min, and then subjected to electrophoresis identification. The correctly identified pAd-sp-E1A-ΔE1B-anti-PD1 plasmid was transformed into DH5α competent cells, and then the cells were spread on the plate. Afterward, several single colonies were picked and cultured with shaking. The plasmid was extracted from the cultured bacterial cells for restriction digestion identification. The restriction digestion system is as follows:

| | |
|---|---|
| pAd-sp-E1A-ΔE1B-anti-PD1 | 8 μL |
| MluI | 1 μL |
| 10 × Buffer | 2 μL |
| ddH$_2$O | 9 μL |
| Total | 20 μL |

The above reaction system was placed in a 37° C. water bath for 30 min, and then subjected to electrophoresis identification.

Package of Recombinant Virus (1) Cell Plating

HEK-293 cells were cultured in a 6-well plate and allowed to reach 60%-80% of cell density the next day.

(2) pAd-sp-E1A-E1B-Anti-PD1 Plasmid was Linearized with PacI Enzyme:

| | |
|---|---|
| pAd-sp-E1A-ΔE1B-anti-PD1 | 1 μg |
| PacI | 1 μL |
| 10 × Buffer | 2 μL |
| ddH$_2$O | up to 20 μL |

The above reaction system was placed in a 37° C. water bath for 2 h.

(3) Plasmid Transfection and Virus Package

According to the instruction of Effectene Transfection Reagent kit (Invitrogen), 1 μg of the above linearized plasmid pAd-sp-E1A-ΔE1B-anti-PD1 was transfected into HEK-293 cells in a 6-well plate. After about 7-10 days when the cells were completely infected and broken by the virus, the supernatant containing virus was collected to obtain the recombinant adenovirus Ad-sp-E1A-ΔE1B-anti-PD1, which was stored at −80° C. for later use.

Identification of Recombinant Virus (1) According to the instruction of blood genome extraction kit (Shanghai Generay Bioengineering Co., Ltd.), the viral genome DNA was extracted.

(2) PCR identification of anti-PD1 gene carried by Ad-sp-E1A-ΔE1B-anti-PD1

The PCR reaction system is as follows:

| | |
|---|---|
| Viral DNA | 1 μL |
| Identification anti-PD 1-F | 1 μL |
| Identification anti-PD 1-R | 1 μL |
| 2 × Taq enzyme | 12.5 μL |
| ddH$_2$O | 9.5 μL |
| Total | 25 μL |

The PCR reaction procedure is as follows:

| | | |
|---|---|---|
| 94° C. pre-denaturation | 5 min | |
| 94° C. denaturation | 30 sec | |
| 55° C. annealing | 30 sec | 30 cycles |
| 72° C. extension | 2 min | |
| 72° C. extension | 5 min | |

The reaction products were stored at 4° C.

After PCR, the products were subjected to 1% agarose gel for electrophoresis identification.

(3) PCR identification for presence or absence of recombinant wild-type virus having wild-type E1A promoter in Ad-sp-E1A-ΔE1B-anti-PD1

The PCR reaction system is as follows:

| | |
|---|---|
| Viral DNA | 1 μL |
| E1A Promotor-F2 | 1 μL |
| E1A Promotor-R2 | 1 μL |
| 2 × Taq enzyme | 12.5 μL |
| ddH$_2$O | 9.5 μL |
| Total | 25 μL |

The PCR reaction procedure is as follows:

| | | |
|---|---|---|
| 94° C. pre-denaturation | 5 min | |
| 94° C. denaturation | 30 sec | |
| 55° C. annealing | 30 sec | 30 cycles |
| 72° C. extension | 1 min | |
| 72° C. extension | 5 min | |

The reaction products were stored at 4° C.

After PCR, the products were subjected to 1% agarose gel for electrophoresis identification.

(4) PCR identification for presence or absence of recombinant wild-type virus having E1B region in Ad-sp-E1A-ΔE1B-anti-PD1

The PCR reaction system is as follows:

| | |
|---|---|
| Viral DNA | 1 μL |
| ΔE1B-F | 1 μL |
| ΔE1B-R | 1 μL |
| 2 × Taq enzyme | 12.5 μL |
| ddH$_2$O | 9.5 μL |
| Total | 25 μL |

The PCR reaction procedure was the same as (3). After PCR, the products were subjected to 1% agarose gel for electrophoresis identification.

Titer Determination of Recombinant Virus

The principle of virus titer determination is to determine the number of viruses with infectious activity based on the number of hexon-stained positive cells by immunocytochemistry. According to the instructions of the adenovirus titer kit, the virus titer of the amplified and purified adenovirus was determined.

Evaluation of Inhibitory Ability of Oncolytic Adenovirus Ad-sp-E1A-ΔE1B-anti-PD1 on Tumors Detection of Virus Toxicity to Cells by CCK8 Method The normal cells or tumor cells were seeded in a 96-well plate. After the cells were fully attached, the recombinant adenovirus to be tested with different MOI was added to each well. After culturing for a certain period of time, 20 μL of CCK8 solution was added to each well, and 4 hours later, the absorbance of each well was detected by a microplate reader. The cell survival rate was calculated based on the formula and the cell survival curve was plotted.

Detection of The Safety of Oncolytic Virus by Crystal Violet Method

The cells were seeded in a 24-well plate. One day later, the cells were infected with the recombinant adenovirus to be tested with appropriate MOI. After 4 days of culture at 37° C., the culture medium was discarded, and 500 μL of crystal violet staining solution (2% crystal violet in 20% methanol solution) was added to each well to stain for 15 min, and then the excess staining solution was washed away with clean water. After staining, cell images were taken.

Real-time Quantitative PCR

I. Extraction of RNA

RNA was extracted according to the instructions of TRIzol Reagent and stored at −80° C. for later use.

II. RNA Reverse Transcription i. Determining RNA Concentration ii. Reverse Transcription System:

| | |
|---|---|
| RNA | 1 μg |
| RT Enzyme Mix | 0.5 μL |
| Primer Mix | 0.5 μL |
| 5 × RT buffer | 2 μL |
| Nuclease-free Water | up to 10 μL |

PCR Reaction Procedure:

| | |
|---|---|
| 37° C. | 15 min |
| 98° C. | 5 min |
| 4° C. | Forever |

III. Specific Steps of q-PCR i. Preparation of q-PCR reaction system:

| | |
|---|---|
| Distilled water | 6.4 μL |
| SYBR Green Master Mix | 10 μL |
| Forward primer (10 μM) | 0.8 μL |
| Reverse primer (10 μM) | 0.8 μL |
| cDNA | 2 μL |
| Total | 20 μL | ii. The above reaction system was added to a 96-well plate. Then the sealing film special for Q-PCR was used to carefully cover the 96-well plate added with samples, and the special card was used to press the film in the same direction, the surface of which should be avoided touching directly by hands.

iii. The 96-well plate was centrifuged at 1000 rpm for 1 min.

iv. Real-time fluorescent quantitative PCR reaction was carried out on Bio-Rad fluorescent quantitative PCR instrument, and the reaction procedure is as follows:

| | | |
|---|---|---|
| (1) 95° C. | pre-denaturation | 5 min |
| (2) 95° C. | denaturation | 10 s |
| (3) 60° C. | annealing and extension | 30 s; plate reading |
| (4) GO TO (2), 39 more cycles | | |
| (5) 95° C. | 15 s | |
| (6) 60° C. | 1 min | |
| (7) melt curve 60.0 to 95.0° C. increment 0.5° C. 15 s; plate reading; END | | |

Western Blot

The expression levels of E1A protein and anti-PD1 protein in tumor cells were detected by Western blot. The specific steps are as follows.

Gel Preparation

Prior to the experiment, a suitable concentration of SDS-polyacrylamide gel was prepared according to the molecular weights of target proteins. The concentration of polyacrylamide separation gel was determined according to the molecular weights of target proteins to be separated and detected, wherein the formulae of 10% separation gel and 4% stacking gel are shown in Table 1.

TABLE 1

| SDS polyacrylamide gel formula | | |
|---|---|---|
| | 10% separation gel (10 ml) | 5% stacking gel (5 ml) |
| Ultra-pure water | 4.0 mL | 3.4 mL |
| 30% Acr/Bic (29:1) | 3.3 mL | 0.83 mL |
| 1.5 mol/L Tris•HCl (pH 8.8) | 2.5 mL | — |
| 0.5 mol/L Tris•HCl (pH 6.8) | — | 0.63 mL |
| 10% SDS | 100 μL | 50 μL |
| 10% AP (Ammonium persulfate) | 100 μL | 50 μL |
| TEMED | 6 μL | 5 μL |

Electrophoresis and Electrotransfer

First, a dust-free paper was used to remove the alcohol between the two plates, and the separation gel was filled, followed by anhydrous alcohol to flatten the interface of the gel. Then, after the separation gel was molded, alcohol was poured off and the remaining was evaporated in a ventilated place. Next, the 5% stacking gel according to the formulae was filled and the 1.5 mm thickness western blot comb (Bio-Rad) was immediately inserted to form the sample slots. The stacking gel was allowed to mold and transferred to the electrophoresis tank, and 1× electrophoresis buffer was added until the tops between the long and short glass plates. Afterward, the comb was removed, and the samples were sequentially loaded into the slots. Electrophoresis at 80/120V was then performed, and ceased until Marker protein migrated to an appropriate position. After the electrophoresis, the stacking gel was cut off, and a piece of PVDF membrane was prepared. Sponge, filter paper, protein gel, and PVDF membrane were placed in the pre-cooled transfer buffer sequentially according to the positive and negative electrodes to perform electrotransfer, and a ice box was put on one side so the entire electrotransfer system was surrounded with ice. Generally, electrotransfer was performed at 90V for 70 min.

Blocking

After the electrotransfer, the PVDF membrane was taken out and marked with a corner sheared, and then blocked with the currently-prepared blocking solution (purchased from BD) for 30 min.

Antibody Incubation

The relevant antibody was diluted with 1% BSA solution in a dilution ratio recommended by the manufacturer's instruction, and then the blocked PVDF membrane was incubated with the diluted antibody with shaking for 2 hours at room temperature (or overnight at 4° C.). Next, the PVDF membrane was washed with 1×TBST buffer for 5 min each time, and repeated for twice. Then the corresponding secondary antibody was diluted with 1% BSA solution in a dilution ratio recommended by the instruction, and then the washed PVDF membrane was incubated with the diluted secondary antibody with shaking at room temperature. After 2 hours of incubation with the secondary antibody, the PVDF membrane was washed with 1×TBST buffer for 5 min each time, and repeated for three times.

Development

A developing ECL solution was dropped on the PVDF membrane after the above treatment, and then the PVDF membrane was exposed and developed under a chemiluminescence imaging system.

MSD Analysis of PD1 Antibody Activity in Cell Culture Supernatants Treated with Virus Carrying PD1 Antibody The PD-1 protein was coated on the bottom of the plate, and then the sample to be tested along with PD-L1 were added. The sample to be tested will compete with PD-L1 to bind to PD-1. PD-L1 was coupled with a sulfo-tag, so the activity of PD1 antibody in the sample to be tested can be estimated by the electrochemiluminescence signal.

In Vivo Tumor Suppression Experiment

In Vivo Tumor Suppression Experiment in Transplanted Tumor Model in Nude Mouse

Inoculation of MDA-MB-231 cells: 3-4 week old mice (nude mice) were ordered. After one week of housing for adaptation, the mice were inoculated subcutaneously with MDA-MB-231 cells at a cell amount of 2 million/mouse, and the tumor size was observed daily. Starting from the 14th day of inoculation, the mice were injected intratumorally with the virus to be tested once every other day with each injection dose of $1.5 \times 10^{10}$ vp, a total of 5 injections, and PBS solution was used as a negative control. Tumor size was measured every two days.

Inoculation of HCC827 cells: 3-4 week old mice (nude mice) were ordered. After one week of housing for adaptation, the mice were inoculated subcutaneously with HCC827 cells at a cell amount of 2 million/mouse, and the tumor size was observed daily. After the tumor grew to 80-100 mm$^3$, the mice were injected intratumorally with the virus to be tested once every other day with each injection dose of $1.5 \times 10^{10}$ vp, a total of 4 injections (Day 0, Day 2, Day 4 and Day 6). PBS solution was used as a negative control and first-line clinical antitumor drugs sorafenib and gemcitabine were used as positive controls. The tumor size was measured every two days.

In Vivo Tumor Suppression Experiments in Humanized Mouse Model

The humanized mouse model was constructed in-house according to the following procedure. Severely immunodeficient NDG or NCG mice were used. When the mice were 3 weeks old, they were fed antibiotics. One week later, the mice were subjected to irradiation and injected with hCD34$^+$ cells on the same day. The mice were continued to be fed antibiotics for two weeks. On the second day after irradiation, the bone marrow of mice was extracted to detect the ratio of mCD45 and mCD117 positive cells to determine the myeloablative effect. In the third week after irradiation, peripheral blood flow cytometry was performed to detect the humanization process of the immune system. 22-week-old humanized mice that had been successfully constructed by humanization of the immune system (the proportion of human CD45+ cell was greater than 15%) were selected, and then injected subcutaneously with $2 \times 10^6$ HCC827 tumor cells for tumor formation. When the tumor size after measurement was about 80 mm$^3$ and the mice were in good health, the mice were randomly divided into three groups for administration with different reagents, namely the PBS group (n=6, intratumoral administration, once every other day, 5 times in total), the PD-1 antibody SSI-361 of Lyvgen Biopharma (Reference can be made to patent application No. CN201680079355.1), which was a positive control group of PD1 antibody (n=6, intraperitoneal injection, injection dose of 10 mg/kg, 2 times a week, 6 times in total), and Ad-sp-E1A-ΔE1B-anti-PD1-3 group (n=6, intratumoral administration, once every other day, $1.5 \times 10^{10}$ vp/time, 5 times in total). The tumor size was observed and measured twice a week.

Example 1

Construction of Adenovirus Ad-sp-E1A-ΔE1B-anti-PD1

First, on the basis of wild-type adenovirus, by deleting the E1B region and replacing the endogenous wild-type promoter of E1A gene, an oncolytic adenovirus Ad-sp-E1A-ΔE1B for dual-targeting of tumor cells with enhanced safety and targeting was constructed. The virus has a tumor-specific survivin promoter to control the expression of the early gene E1A of adenovirus, and the adenovirus, after knocking out the early gene E1B region, will preferably replicate in cancer cells without p53 function.

On this basis, the expression cassette containing the PD1 single-chain antibody (anti-PD1) and driven by human CMV promoter was inserted into the BglII site of the aforementioned adenovirus Ad-sp-E1A-ΔE1B to construct a recombinant oncolytic adenovirus carrying anti-PD1 gene.

As shown in FIG. 1, Ad-sp-E1A-ΔE1B is an no-load virus with no PD1 antibody sequence. Ad-sp-E1A-ΔE1B-FL is a recombinant oncolytic virus expressing the full-length PD-1 antibody, formed by inserting the light chain sequence as shown in SEQ ID NO: 1 at the XhoI site as well as the heavy chain sequence as shown in SEQ ID NO: 2 at the BglII site.

Ad-sp-E1A-ΔE1B-anti-PD1-1 and Ad-sp-E1A-ΔE1B-anti-PD1-2 both contain the single-chain antibody in which the heavy chain variable region as shown in SEQ ID NO: 3 and the light chain variable region as shown in SEQ ID NO: 4 were linked through a (Gly$_4$Ser)$_6$ linker. For the single-chain antibody of Ad-sp-E1A-ΔE1B-anti-PD1-1, the light chain variable region is at the N-terminus (i.e., VL-VH), wherein the amino acid sequence of the single-chain antibody is shown in SEQ ID NO: 5 and the coding sequence of that is shown in SEQ ID NO: 6. For the single-chain antibody of Ad-sp-E1A-ΔE1B-anti-PD1-2, the heavy chain variable region is at the N-terminus (i.e., VH-VL), wherein the amino acid sequence of the single-chain antibody is shown in SEQ ID NO: 7 and the coding sequence of that is shown in SEQ ID NO: 8.

The Light Chain Sequence:

```
                                     (SEQ ID NO: 1)
MDMRVPAQLLGLLLLWFPGSRCDIQMTQSPSSLSA

SVGDRVTITCRAGQNVQNYLAWYQQKPGKAPKVLI

FNAQSLQTGVPSRFSGSGSGTDFTLTISSLQPEDF

ATYYCQQYNSWPTFGGGTKVEIKRTVAAPSVFIFP

PSDEQLKSGTASVVCLLNNFYPREAKVQWKVDNAL

QSGNSQESVTEQDSKDSTYSLSSTLTLSKADYEKH

KVYACEVTHQGLSSPVTKSFNRGEC.
```

The Heavy Chain Sequence:

```
                                     (SEQ ID NO: 2)
MDMRVPAQLLGLLLLWLPGARCQVTLKESGPALVK

PTQTLTLTCTFSGFSLSTSGTCVSWIRQPPGKALE

WLATICWEDSKGYSTSLKSRLTISKDTSKNQAVLT

MTNMDPVDTATYYCARREDSGYFWFPYWGQGTLVT

VSSASTKGPSVFPLAPCSRSTSESTAALGCLVKDY

FPEPVTVSWNSGALTSGVHTFPAVLQSSGLYSLSS

VVTVPSSSLGTKTYTCNVDHKPSNTKVDKRVESKY

GPPCPPCPAPEFLGGPSVFLFPPKPKDTLMISRTP

EVTCVVVDVSQEDPEVQFNWYVDGVEVHNAKTKPR
```

-continued
EEQFNSTYRVVSVLTVLHQDWLNGKEYKCKVSNKG

LPSSIEKTISKAKGQPREPQVYTLPPSQEEMTKNQ

VSLTCLVKGFYPSDIAVEWESNGQPENNYKTTPPV

LDSDGSFFLYSRLTVDKSRWQEGNVFSCSVMHEAL

HNHYTQKSLSLSLGK.

The Heavy Chain Variable Region:

(SEQ ID NO: 3)
QVTLKESGPALVKPTQTLTLTCTFS GFSLSTSGT CVSWIRQPPGKALEW

LATI CWEDS KGYSTSLKSRLTISKDTSKNQAVLTMTNMDPVDTATYYCA

RR EDSGYFWFPY WGQGTLVTVSS.

The three complementarity determining region (CDR) sequences in the heavy chain variable region are listed in the box.

The Light Chain Variable Region:

(SEQ ID NO: 4)
DIQMTQSPSSLSASVGDRVTITC RAGQNVQNYLA WYQQKPGKAPKVLIF

NAQSLQT GVPSRFSGSGSGTDFTLTISSLQPEDFATYYC QQYNSWPT FG

GGTKVEIK.

The three complementarity determining region (CDR) sequences in the light chain variable region are listed in the box.

The amino acid sequence of the single-chain antibody (anti-PD1-1) in Ad-sp-E1A-ΔE1B-anti-PD1-1:

(SEQ ID NO: 5)
MDMRVPAQLLGLLLLWFPGSRC DIQMTQSPSSLSASVGDRVTITCRAGQ

NVQNYLAWYQQKPGKAPKVLIFNAQSLQTGVPSRFSGSGSGTDFTLTIS

SLQPEDFATYYCQQYNSWPTFGGGTKVEIK GGGGSGGGGSGGGGSGGGG

SGGGGSGGGGS QVTLKESGPALVKPTQTLTLTCTFSGFSLSTSGTCVSW

IRQPPGKALEWLATICWEDSKGYSTSLKSRLTISKDTSKNQAVLTMTNM

DPVDTATYYCARREDSGYFWFPYWGQGTLVTVSS.

The signal peptide sequence is listed in the box, and the linker peptide sequence is underlined.

The coding sequence of the single-chain antibody (anti-PD1-1) in Ad-sp-E1A-ΔE1B-anti-PD1-1:

(SEQ ID NO: 6)
ATGGATATGAGAGTACCAGCTCAGCTGCTGGGCCT

GCTGCTCCTGTGGTTCCCTGGCAGCCGGTGCGACA

TCCAGATGACGCAGAGCCCCTCCAGTCTCTCTGCT

AGCGTGGGCGACAGGGTCACAATTACATGCAGAGC

-continued
TGGACAGAACGTCCAGAATTATTTGGCCTGGTACC

AGCAGAAACCTGGAAAGGCTCCAAAGGTGTTGATC

TTCAATGCGCAATCTCTCCAAACAGGCGTGCCCTC

CCGCTTCTCCGGCTCAGGGTCTGGCACCGACTTTA

CCCTTACCATCTCTAGCCTTCAGCCTGAGGATTTT

GCTACTTACTACTGTCAGCAGTATAATTCCTGGCC

TACATTTGGTGGTGGTACGAAAGTCGAGATTAAGG

GTGGTGGAGGTTCTGGAGGAGGTGGAAGTGGTGGC

GGAGGAAGCGGCGGTGGTGGTTCAGGAGGGGGAGG

GTCAGGGGGGGGAGGCTCCCAAGTTACACTCAAGG

AAAGCGGTCCGGCCCTTGTAAAGCCCACCCAGACA

CTGACTCTGACCTGTACATTCAGCGGCTTCAGCCT

GTCAACGTCCGGCACATGTGTTAGCTGGATACGCC

AGCCCCCGGGGAAAGCACTGGAGTGGCTCGCGACC

ATCTGCTGGGAAGATAGTAAAGGGTACTCTACAAG

CCTTAAATCACGCCTGACCATTTCAAAGGATACTA

GTAAGAATCAGGCCGTCCTTACAATGACCAATATG

GATCCCGTCGACACTGCAACATACTATTGTGCCCG

CCGGGAAGATAGCGGATACTTCTGGTTCCCCTACT

GGGGCCAAGGAACTCTCGTGACAGTCAGTTCCTAA.

The amino acid sequence of the single-chain antibody (anti-PD1-2) in Ad-sp-E1A-ΔE1B-anti-PD1-2

(SEQ ID NO: 7)
MDMRVPAQLLGLLLLWLPGARC QVTLKESGPALVKPTQTLTLTCTFSGF

SLSTSGTCVSWIRQPPGKALEWLATICWEDSKGYSTSLKSRLTISKDTS

KNQAVLTMTNMDPVDTATYYCARREDSGYFWFPYWGQGTLVTVSS GGGG

SGGGGSGGGGSGGGGSGGGGSGGGGS DIQMTQSPSSLSASVGDRVTITC

RAGQNVQNYLAWYQQKPGKAPKVLIFNAQSLQTGVPSRFSGSGSGTDFT

LTISSLQPEDFATYYCQQYNSWPTFGGGTKVEIK.

The signal peptide sequence is listed in the box, and the linker peptide sequence is underlined.

The coding sequence of the single-chain antibody (anti-PD1-2) in Ad-sp-E1A-ΔE1B-anti-PD1-2:

(SEQ ID NO: 8)
ATGGACATGAGAGTCCCAGCCCAGCTGCTTGGTCT

GTTGCTTCTCTGGCTCCCGGGTGCCCGCTGCCAGG

TGACGCTGAAGGAGTCAGGCCCTGCCTTGGTTAAG

CCCACCCAGACCCTGACCCTCACATGTACCTTCTC

CGGGTTCTCATTGTCAACCTCCGGCACTTGTGTCA

GTTGGATCAGGCAACCCCCTGGCAAAGCCCTTGAG

TGGTTGGCTACGATTTGCTGGGAAGACAGTAAAGG

-continued

ATACTCAACAAGCCTCAAATCTCGGCTGACCATTA

GTAAAGATACATCCAAGAACCAGGCAGTCCTTACC

ATGACCAATATGGACCCAGTCGATACCGCCACCTA

CTATTGCGCTCGCCGAGAGGATTCTGGCTACTTCT

GGTTCCCATATTGGGGCCAAGGAACACTTGTGACC

GTATCAAGTGGTGGAGGGGGTAGCGGTGGAGGTGG

AAGTGGTGGCGGAGGAAGTGGCGGAGGTGGGTCCG

GAGGCGGCGGCTCCGGAGGAGGTGGTTCAGATATT

CAGATGACCCAGTCCCCCAGCTCTCTGAGTGCATC

CGTCGGCGATAGAGTGACTATCACATGTCGAGCCG

GACAGAACGTGCAAAATTACCTGGCCTGGTACCAG

CAGAAGCCGGGTAAGGCTCCCAAAGTGCTTATTTT

CAATGCCCAATCTCTGCAGACCGGGGTGCCAAGCC

GGTTTAGTGGTTCTGGCTCCGGTACTGACTTCACG

CTTACCATTTCCAGTCTGCAACCGGAGGATTTCGC

TACATATTACTGCCAGCAGTACAACAGCTGGCCAA

CCTTCGGGACAAAAGTTGAAATCAAGTAA.

Ad-sp-E1A-ΔE1B-anti-PD1-3 and Ad-sp-E1A-ΔE1B-anti-PD1-4 both contain the single-chain antibody in which the heavy chain variable region as shown in SEQ ID NO: 3 and the light chain variable region as shown in SEQ ID NO: 4 were linked through a (Gly₄Ser)₆ linker, followed by the antibody Fc fragment (SEQ ID NO: 9) fused to the C-terminus. For the single-chain antibody of Ad-sp-E1A-ΔE1B-anti-PD1-3, the light chain variable region is at the N-terminus (i.e., VL-VH), wherein the amino acid sequence of the single-chain antibody fused with the Fc fragment is shown in SEQ ID NO: 10 and the coding sequence of that is shown in SEQ ID NO: 11. For the single-chain antibody of Ad-sp-E1A-ΔE1B-anti-PD1-4, the heavy chain variable region is at the N-terminus (i.e., VH-VL), wherein the amino acid sequence of the single-chain antibody fused with the Fc fragment is shown in SEQ ID NO: 12 and the coding sequence of that is shown in SEQ ID NO: 13.

The Amino Acid Sequence of the Immunoglobulin Fc Fragment:

(SEQ ID NO: 9)
ASTKGPSVFPLAPCSRSTSESTAALGCLVKDYFPE

PVTVSWNSGALTSGVHTFPAVLQSSGLYSLSSVVT

VPSSSLGTKTYTCNVIDEIKPSNTKVDKRVESKYG

PPCPPCPAPEFLGGPSVFLFPPKPKDTLMISRTPE

VTCVVVDVSQEDPEVQFNWYVDGVEVHNAKTKPRE

EQFNSTYRVVSVLTVLHQDWLNGKEYKCKVSNKGL

PSSIEKTISKAKGQPREPQVYTLPPSQEEMTKNQV

SLTCLVKGFYPSDIAVEWESNGQPENNYKTTPPVL

DSDGSFFLYSRLTVDKSRWQEGNVFSCSVMHEALH

NHYTQKSLSLSLGK.

The amino acid sequence of the single-chain antibody+Fc (anti-PD1-3) in Ad-sp-E1A-ΔE1B-anti-PD1-3:

(SEQ ID NO: 10)
MDMRVPAQLLGLLLLWFPGSRCDIQMTQSPSSLSASVGDRVTITCRAGQ

NVQNYLAWYQQKPGKAPKVLIFNAQSLQTGVPSRFSGSGSGTDFTLTIS

SLQPEDFATYYCQQYNSWPTFGGGTKVEIKGGGGSGGGGSGGGGSGGGG

SGGGGSGGGGSQVTLKESGPALVKPTQTLTLTCTFSGFSLSTSGTCVSW

IRQPPGKALEWLATICWEDSKGYSTSLKSRLTISKIDTSKNQAVLTMTN

MDPVDTATYYCARREDSGYFWFPYWGQGTLVTVSSASTKGPSVFPLAPC

SRSTSESTAALGCLVKDYFPEPVTVSWNSGALTSGVHTFPAVLQSSGLY

SLSSVNTVPSSSLGTKTYTCNVDHKPSNTKVDKRVESKYGPPCPPCPAP

EFLGGPSVFLFPPKPKDTLMISRTPEVTCVVVDVSQEDPEVQFNWYVDG

VEVHNAKTKPREEQFNSTYRVVSVLTVLHQDWLNGKEYKCKVSNKGLPS

SIEKTISKAKGQPREPQVVTLPPSQEEMTKNQVSLTCLVKGFYPSDIAV

EWESNGQPENNYKTTPPVLDSDGSFFLYSRLTVDKSRWQEGNVFSCSVM

HEALHNHYTQKSLSLSLGK.

The signal peptide sequence is listed in the box, the linker peptide sequence is underlined, and the immunoglobulin Fc fragment sequence is shaded.

The nucleotide coding sequence of the single-chain antibody+Fc (anti-PD1-3) in Ad-sp-E1A-ΔE1B-anti-PD1-3:

(SEQ ID NO: 11)
ATGGATATGCGGGTGCCGGCACAGCTGTTGGGGCT

GCTGCTCCTCTGGTTTCCTGGCTCACGCTGCGATA

TCCAGATGACTCAGAGTCCCAGTTCCCTGTCTGCC

TCTGTGGGCGATAGAGTCACCATAACCTGTCGCGC

CGGACAAAACGTCCAAAATTACCTGGCGTGGTACC

AGCAGAAACCAGGAAAGGCCCCAAAGGTCCTGATT

TTCAATGCTCAAAGCCTCCAGACTGGAGTCCCCAG

CCGGTTCTCTGGCTCCGGATCTGGCACCGACTTTA

CCTTGACCATCAGCAGCCTGCAGCCCGAGGATTTC

GCAACCTACTATTGTCAGCAGTATAATAGCTGGCC

AACATTCGGGGCGGCACTAAAGTCGAGATCAAGG

GTGGAGGAGGCTCTGGTGGCGGGGGCTCAGGGGGA

GGAGGAAGCGGTGGCGGTGGTTCTGGCGGAGGTGG

```
-continued
CAGTGGTGGTGGCGGTAGCCAAGTAACCTTGAAGG
AGTCCGGTCCCGCACTGGTGAAACCCACACAAACG
CTTACGCTCACTTGTACCTTCAGCGGTTTTAGCCT
GTCTACGTCCGGAACCTGCGTTTCTTGGATCCGGC
AGCCTCCCGGCAAGGCCCTCGAGTGGCTGGCCACC
ATCTGCTGGGAAGACTCCAAAGGTTACTCAACCAG
TCTTAAAAGTAGGTTGACAATCAGCAAGGATACCA
GTAAAAATCAGGCAGTTCTTACCATGACAAACATG
GATCCCGTAGATACAGCTACCTACTATTGTGCCAG
GCGAGAAGACTCCGGTTACTTTTGGTTCCCCTACT
GGGGTCAGGGGACTCTGGTCACGGTCAGCTCTGCC
TCCACCAAGGGCCCTTCTGTGTTCCCCCTGGCACC
ATGTAGCCGGTCCACCTCCGAGAGCACTGCAGCGT
TGGGCTGCTTGGTGAAAGACTATTTTCCCGAGCCT
GTAACTGTGAGTTGGAACAGCGGCGCCCTCACGAG
CGGGGTGCACACCTTTCCCGCAGTCTTGCAGAGCT
CCGGTCTCTATTCCCTTTCTAGTGTTGTTACCGTG
CCGAGCAGCTCTCTTGGCACCAAGACTTACACCTG
CAATGTTGACCATAAACCGTCTAATACTAAAGTTG
ACAAGAGGGTCGAGAGCAAATACGGCCCACCATGC
CCACCTTGCCCAGCACCTGAGTTCCTGGGCGGCCC
CTCAGTGTTCTTGTTTCCCCCAAAGCCTAAAGACA
CCCTGATGATTAGCCGACACCCGAGGTGACTTGC
GTCGTGGTCGATGTGAGTCAGGAAGACCCTGAAGT
GCAGTTCAACTGGTATGTAGACGGGGTTGAGGTAC
ACAACGCAAAGACTAAACCACGCGAGGAACAGTTT
AATAGTACGTACCGGGTGGTGTCCGTGCTTACAGT
CCTGCACCAGGATTGGTTGAATGGAAAGGAATATA
AGTGCAAAGTGAGCAATAAAGGCCTGCCTTCTTCT
ATCGAGAAGACAATATCCAAAGCAAAAGGTCAACC
TCGGGAGCCTCAGGTGTATACCTTGCCCCCGAGCC
AGGAGGAAATGACGAAAAATCAGGTTAGTCTGACG
TGTCTTGTGAAGGGCTTTTACCCATCTGATATCGC
AGTGGAGTGGGAAAGCAACGGGCAGCCCGAGAATA
ACTATAAGACGACCCCGCCCGTCCTGGACTCAGAT
GGTAGCTTCTTCCTGTATTCCCGCCTGACAGTTGA
CAAATCTCGCTGGCAAGAAGGAAATGTTTTTCCT
GCAGTGTCATGCATGAAGCCCTGCACAACCATTAC
ACACAGAAAAGCTTGAGCCTGAGTCTGGGGAAGTG
A.
```

The amino acid sequence of the single-chain antibody+Fc (anti-PD1-4) in Ad-sp-E1A-ΔE1B-anti-PD1-4:

(SEQ ID NO: 12)
MDMRVPAQLLGLLLLWLPGARCQVTLKESGPALVKPTQTLTLTCTFSGF

SLSTSGTCVSWIRQPPGKALEWLATICWEDSKGYSTSLKSRLTISKDTS

KNQAVLTMTNMDPVDTATYYCARREDSGYFWFPYWGQGTLVTVSSGGGG

SGGGGSGGGGSGGGGSGGGGSGGGGSDIQMTQSPSSLSASVGDRVTITC

RAGQNVQNYLAWYQQKPGKAPKVLIFNAQSLQTGVPSRFSGSGSGTDFT

LTISSLQPEDFATYYCQQYNSWPTFGGGTKVEIKASTKGPSVFPLAPCS

RSTSESTAALGCLVKDYFPEPVTVSWNSGALTSGVHTFPAVLQSSGLYS

LSSVVTVPSSSLGTKTYTCNVDHKPSNTKVDKRVESKYGPPCPPCPAPE

FLGGPSVFLFPPKPKDTLMISRTPEVTCVVVDVSQEDPEVQFNWYVDGV

EVHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAVE

WESNGQPENNYKTTPPVLDSDGSFFLYSRLTVDKSRWQEGNVFSCSVMH

EALHNHYTQKSLSLSLGK.

The signal peptide sequence is listed in the box, the linker peptide sequence is underlined, and the immunoglobulin Fc fragment sequence is shaded.

The nucleotide coding sequence of the single-chain antibody+Fc (anti-PD1-4) in Ad-sp-E1A-ΔE1B-anti-PD1-4:

```
(SEQ ID NO: 13)
ATGGACATGCGGGTCCCCGCTCAACTGCTGGGCCT

TCTTTTGCTCTGGTTGCCGGGTGCAAGATGCCAGG

TAACCCTGAAAGAATCCGGACCGGCCTTGGTAAAG

CCGACGCAGACCCTTACTCTCACATGTACGTTTAG

TGGATTCTCATTGTCTACATCAGGAACATGTGTCA

GCTGGATCCGGCAGCCGCCCGGTAAAGCCCTGGAG

TGGCTTGCCACAATATGTTGGGAGGATAGCAAAGG

ATACTCCACAAGTCTTAAGAGTCGCCTGACTATTA

GCAAAGACACGTCCAAGAATCAGGCCGTGCTCACC

ATGACCAATATGGACCCAGTAGATACTGCGACCTA

CTATTGCGCTAGACGGGAAGATTCAGGGTACTTCT

GGTTCCCTTACTGGGGACAGGGGACTCTGGTTACC

GTGTCATCTGGTGGAGGGGGTAGCGGTGGAGGTGG

AAGTGGTGGCGGAGGAAGTGGCGGAGGTGGGTCCG

GAGGCGGCGGCTCCGGAGGAGGTGGTTCAGATATT

CAGATGACACAGAGCCCTTCTTCACTTAGTGCCTC
```

```
-continued
AGTAGGGGACCGCGTCACTATCACATGCCGGGCCG

GGCAGAACGTGCAGAACTACTTGGCTTGGTATCAG

CAGAAGCCCGGAAAAGCGCCCAAAGTGCTGATCTT

CAACGCTCAGTCACTGCAGACTGGAGTGCCTTCCA

GGTTTTCTGGTAGCGGCTCTGGGACCGATTTCACA

CTCACAATCTCTTCTCTGCAGCCAGAGGACTTCGC

CACTTACTACTGCCAACAGTACAATTCCTGGCCTA

CTTTTGGTGGAGGGACAAAGGTAGAGATTAAAGCA

AGTACCAAAGGACCATCTGTCTTCCCTCTGGCACC

ATGCAGCCGGAGCACCAGCGAGTCTACCGCTGCGC

TCGGCTGCCTTGTGAAGGACTACTTCCCAGAACCT

GTGACTGTGTCATGGAATAGCGGCGCTCTGACCAG

TGGAGTTCACACCTTCCCCGCTGTCCTGCAGAGCA

GCGGATTGTACTCTCTCTCCAGCGTGGTGACCGTG

CCCAGTTCCTCCCTCGGTACTAAGACGTATACATG

CAATGTGGACCACAAGCCCTCCAATACCAAGGTCG

ACAAGCGGGTAGAATCAAAATATGGGCCGCCTTGT

CCCCCCTGCCCTGCTCCTGAGTTTCTCGGAGGGCC

CAGCGTCTTCCTCTTTCCACCTAAGCCAAAAGATA

CACTGATGATCTCCCGGACCCCGGAGGTGACATGT

GTGGTGGTGGATGTGTCCCAGGAGGATCCTGAGGT

GCAGTTTAACTGGTACGTCGACGGAGTCGAAGTAC

ACAACGCCAAGACGAAGCCCCGAGAGGAACAGTTT

AATAGTACCTATAGAGTCGTCAGTGTGTTGACCGT

TCTTCATCAGGATTGGCTGAATGGGAAAGAATATA

AATGCAAGGTTTCCAATAAAGGACTCCCATCCTCA

ATCGAGAAAACCATTAGCAAAGCCAAAGGACAGCC

AAGAGAGCCCCAAGTCTACACGCTGCCCCCTTCAC

AGGAAGAGATGACCAAAAACCAGGTTTCCCTTACC

TGCTTGGTGAAGGGCTTTTACCCTTCAGATATCGC

GGTGGAGTGGGAGAGCAATGGGCAGCCCGAGAATA

ATTACAAAACAACGCCGCCAGTGCTTGATTCAGAC

GGCTCATTTTTCCTGTACTCTCGACTGACTGTGGA

CAAAAGCAGGTGGCAGGAGGGGAATGTTTTCTCTT

GTTCTGTGATGCATGAGGCTCTCCACAACCACTAC

ACACAAAAGTCACTGTCCTTGAGCCTCGGCAAGTA

A.
```

Since antibodies need to be secreted outside the cell to function, all of the above single-chain antibodies carry a secretion signal peptide (SEQ ID NO: 14 or 16) at the N-terminus, where the signal peptide shown in SEQ ID NO: 14 is linked before $V_H$, and the signal peptide shown in SEQ ID NO: 16 is linked before $V_L$. All DNA sequences of single-chain antibodies are obtained by direct whole gene synthesis and then directly loaded into a shuttle plasmid.

The Signal Peptide Sequence:

```
                                        (SEQ ID NO: 14)
                    MDMRVPAQLLGLLLLWLPGARC,
or
                                        (SEQ ID NO: 16)
                    MDMRVPAQLLGLLLLWFPGSRC.
```

The Linker Peptide Sequence:

```
                                        (SEQ ID NO: 15)
          GGGGSGGGGSGGGGSGGGGSGGGGSGGGGS.
```

Example 2

Figure 2:
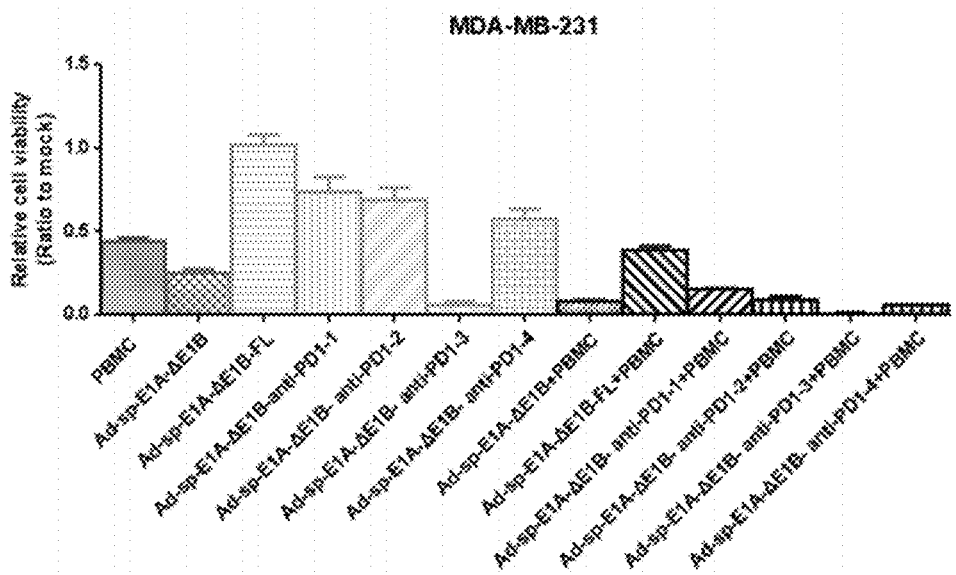
FIG. 2 shows the in vitro killing effects of recombinant oncolytic adenoviruses with different antibody sequences.
Figure 2:
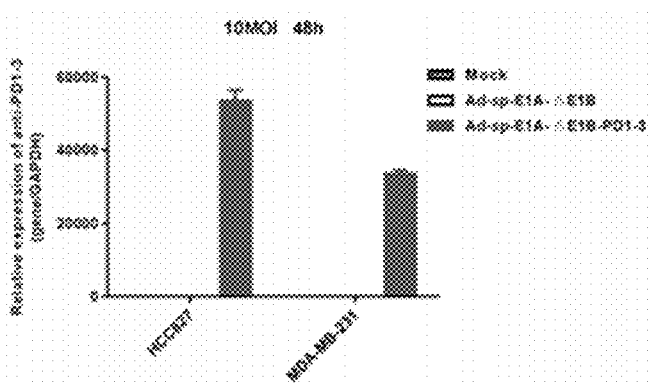
Figure 2:
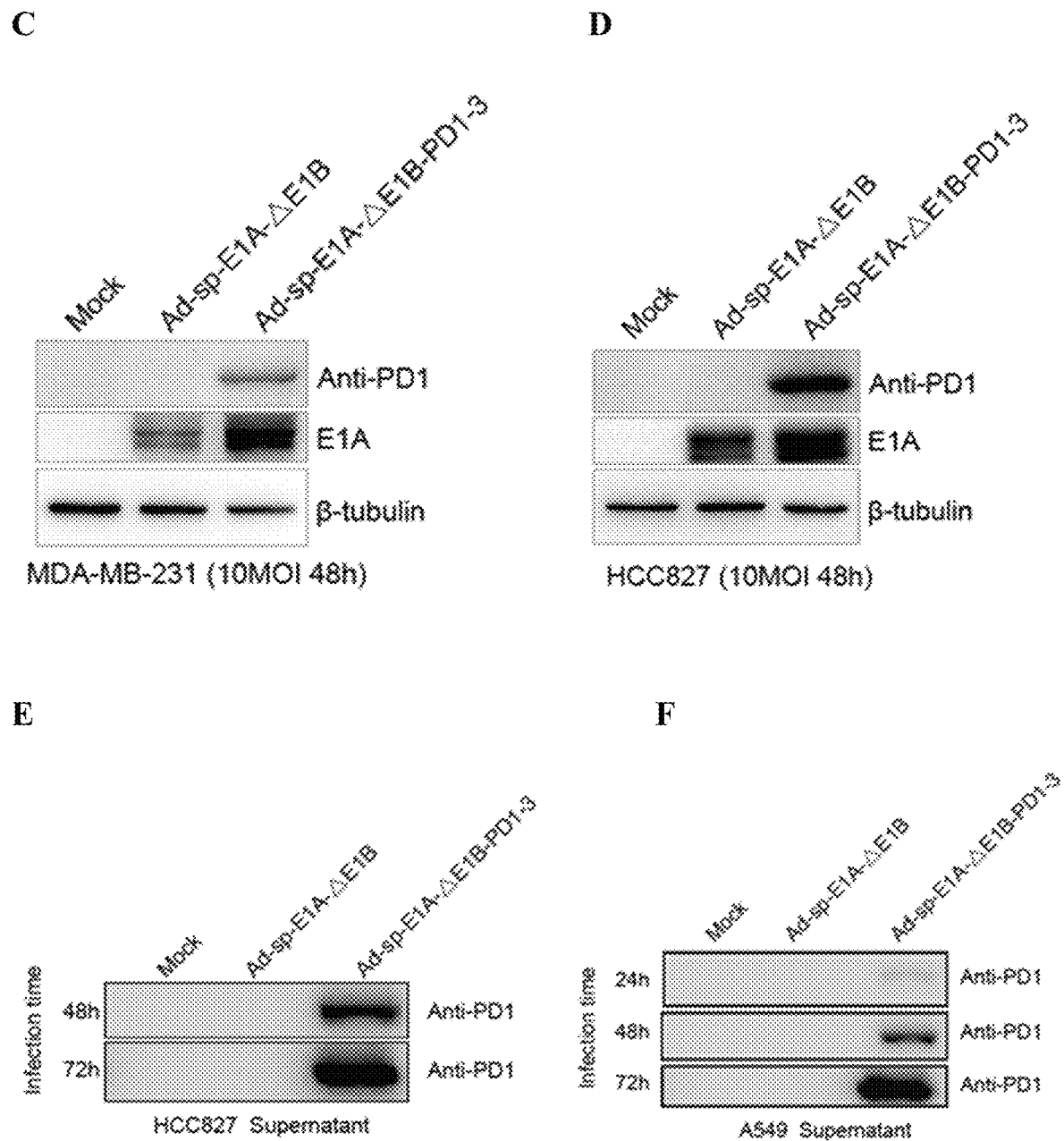

Recombinant Oncolytic Adenovirus Ad-sp-E1A-ΔE1B-anti-PD1-3 Showing the Strongest In Vitro Killing Effect on Cancer Cells In order to compare the killing effects of the recombinant oncolytic adenoviruses carrying various single-chain antibodies or full-length antibodies on tumors, the human breast cancer cell line MDA-MB-231 was selected as the test cell. The above recombinant viruses and the corresponding no-load viruses were used to kill the test cells under same MOI (20 MOI). The results showed that the recombinant oncolytic adenovirus Ad-sp-E1A-ΔE1B-anti-PD1-3 had the best killing ability (as shown in FIG. 2A), and its killing rate on tumor cells reached more than 90%.

Due to the important role of PD1 in immune regulation, peripheral blood mononuclear cells (PBMC) were further added to the test system. The results showed that the recombinant oncolytic adenoviruses showed stronger killing effect in the presence of peripheral blood mononuclear cells (PBMC) (that is, in an immune environment). The recombinant oncolytic adenovirus Ad-sp-E1A-ΔE1B-anti-PD1-3 still showed the best killing ability, and incredibly, it almost achieved complete suppression of tumor cells (FIG. 2A).

The expression of E1A and anti-PD1 after Ad-sp-E1A-ΔE1B-anti-PD1-3 treatment was further detected by Q-PCR and Western Bolt. The results showed that the adenovirus Ad-sp-E1A-ΔE1B-anti-PD1-3 expressed E1A and exogenous PD-1 single-chain antibody (anti-PD1-3) at high levels, both at the transcription level (FIG. 2B) and at the protein level (FIGS. 2C and D), indicating that the anti-PD1-3 gene expression cassette inserted into the adenovirus can be transcribed and translated normally. And with the continuous replication and proliferation of adenovirus, the expression of PD-1 single-chain antibody also increased rapidly (FIGS. 2E and F), which is more conducive to the physiological role of PD-1 single-chain antibody, and other methods such as in vitro transfection cannot achieve the above-mentioned increase in expression over time.

Later, the recombinant oncolytic adenovirus Ad-sp-E1A-ΔE1B-anti-PD1-3 was deposited at China Center for Type Culture Collection (CCTCC, Address: 299 Bayi Road, Wuchang District, Wuhan City, Hubei Province, P.R. China, Post Code: 430072) on Aug. 21, 2018 with a deposit name of Recombinant Human Type 5 Adenovirus Ad-sp-E1A-AE1B-anti-PD1-3, under the accession number CCTCC NO: V201853.

Example 3

Figure 3:
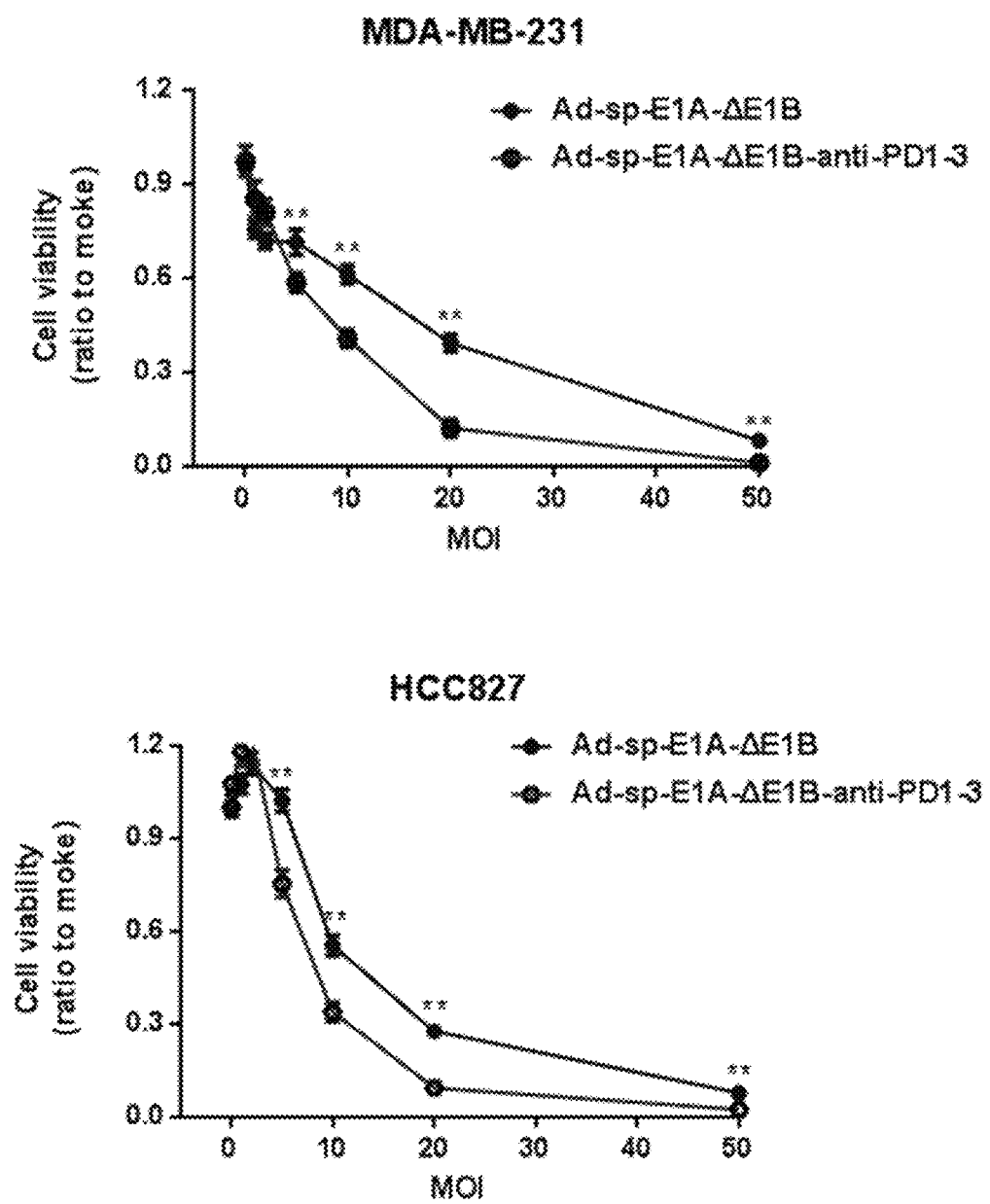
FIG. 3 shows the comparison of the tumor cells killing ability of recombinant oncolytic adenovirus Ad-sp-E1A-ΔE1B-anti-PD1-3 and no-load virus Ad-sp-E1A-ΔE1B.

Recombinant Oncolytic Adenovirus Ad-sp-E1A-ΔE1B-anti-PD1-3 Showing Better In Vitro Killing Effect than Oncolytic Adenovirus without PD1 Antibody The killing ability of the recombinant oncolytic adenovirus Ad-sp-E1A-ΔE1B-anti-PD1-3 and the no-load virus Ad-sp-E1A-ΔE1B on tumor cells was further tested. Specifically, the CCK8 method was used to detect the effects of the two viruses on the breast cancer cell line MDA-MB-231 and the lung cancer cell line HCC827 under different multiplicity of infection (MOI). The results are shown in FIG. 3 that the $IC_{50}$ values of killing effects of Ad-sp-E1A-ΔE1B-anti-PD1-3 on MDA-MB-231 and HCC827 cells were 8.63 MOI and 6.56 MOI, respectively, which were lower than that of the no-load virus Ad-sp-E1A-ΔE1B of 14.03 MOI and 10.20 MOI, respectively, indicating that Ad-sp-E1A-ΔE1B-anti-PD1-3 had a better in vitro killing effect on MDA-MB-231 and HCC827, and that the insertion of PD1 antibody expression sequence can significantly increase the killing effect of oncolytic virus on cancer cells.

Example 4

Figure 4:
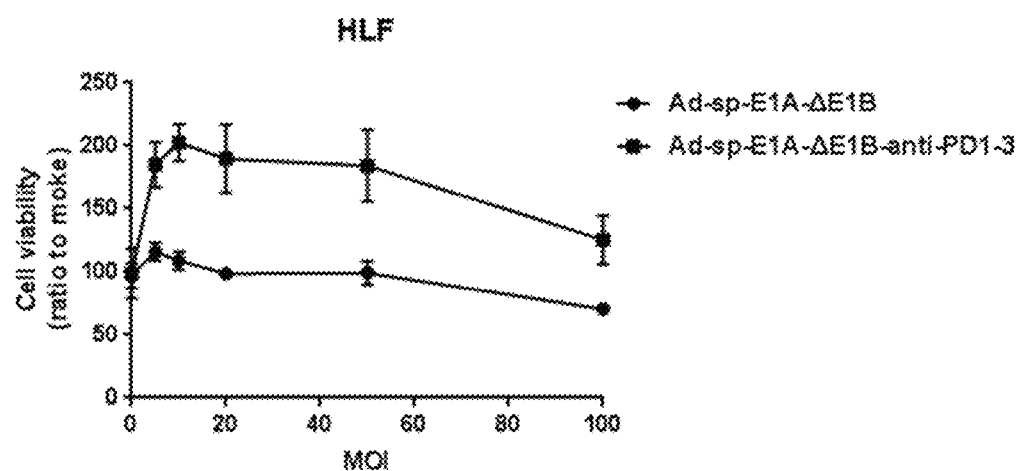
FIG. 4 shows the safety test results of the recombinant oncolytic adenovirus Ad-sp-E1A-ΔE1B-anti-PD1-3 on normal cells.
Figure 4:
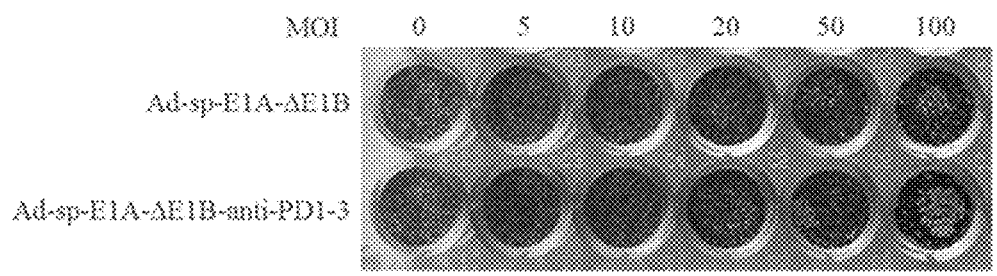

Recombinant Oncolytic Adenovirus Ad-sp-E1A-ΔE1B-anti-PD1-3 Showing Similar Safety as No-Load Virus In order to test the safety of the recombinant oncolytic adenovirus Ad-sp-E1A-ΔE1B-anti-PD1-3 on normal cells, the MTT method was used to detect the killing effects of Ad-sp-E1A-ΔE1B-anti-PD1-3 and the corresponding no-load adenovirus on normal human liver fibroblasts HLF. The results are shown in FIG. 4A that both Ad-sp-E1A-ΔE1B-anti-PD1-3 and the corresponding no-load virus showed good safety that normal cells were hardly killed when treated with up to 100 MOI. What's more unexpected is that Ad-sp-E1A-ΔE1B-anti-PD1-3 is even safer to normal cells than the corresponding no-load virus.

In order to further confirm the good safety of recombinant oncolytic adenovirus Ad-sp-E1A-ΔE1B-anti-PD1-3 against normal cells, the crystal violet method was used as well to detect the killing effects of Ad-sp-E1A-ΔE1B-anti-PD1-3 and the corresponding no-load virus on normal human liver fibroblasts HLF. The results are shown in FIG. 4B that both Ad-sp-E1A-ΔE1B-anti-PD1-3 and the corresponding no-load viruses showed good safety against normal cells.

It can be seen from the results of Examples 2-4 that the recombinant oncolytic adenovirus Ad-sp-E1A-ΔE1B-anti-PD1-3 has excellent in vitro drug efficacy and safety.

Example 5

Recombinant Oncolytic Adenovirus Ad-sp-E1A-ΔE1B-anti-PD1-3 Secretes Active PD1 Antibody from Infected Cells In Vitro Since PD1 antibody works in vivo by blocking the binding of PD1 to the PD1 receptor on the cell surface outside the cell, the prerequisite for the recombinant oncolytic virus Ad-sp-E1A-ΔE1B-anti-PD1-3 to exert maximum efficacy in vivo is that the expressed PD1 antibody can be secreted to the outside of the cell. Therefore, when constructing recombinant oncolytic adenovirus (including Ad-sp-E1A-ΔE1B-anti-PD1-3), a secretion signal peptide was added to the N-terminal of the single-chain antibody to ensure that the expressed PD1 single-chain antibody can be secreted to the outside of the cell to exert a biological effect when administered in vivo.

In order to verify whether the above purposes can be achieved, MSD technique was used to detect the presence of biologically active PD1 single-chain antibody in the cell supernatant infected with the recombinant oncolytic adenovirus Ad-sp-E1A-ΔE1B-anti-PD1-3. The principle of this method is mainly to use PD1 single-chain antibody to compete with PD-L1 to bind to PD-1. PD-1 was coated on the bottom of the plate, and then the supernatant to be tested along with PD-L1 were added to competitively bind to PD-1, with PD-L1 fluorescently labeled with sulfo-tag. By detecting the intensity of the fluorescence signal, the biological activity of PD1 antibody in the supernatant to be tested could be inferred.

Figure 5:
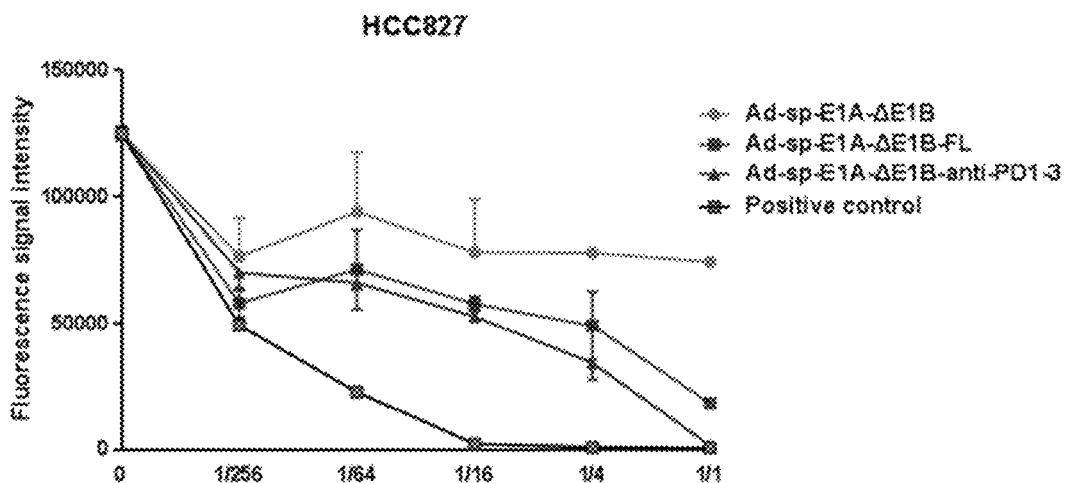
FIG. 5 shows the PD1 antibody secretion in the cell supernatants after Ad-sp-E1A-ΔE1B-anti-PD1-3 infection of HCC827 cells (A) and MDA-MB-231 cells (B).
Figure 5:
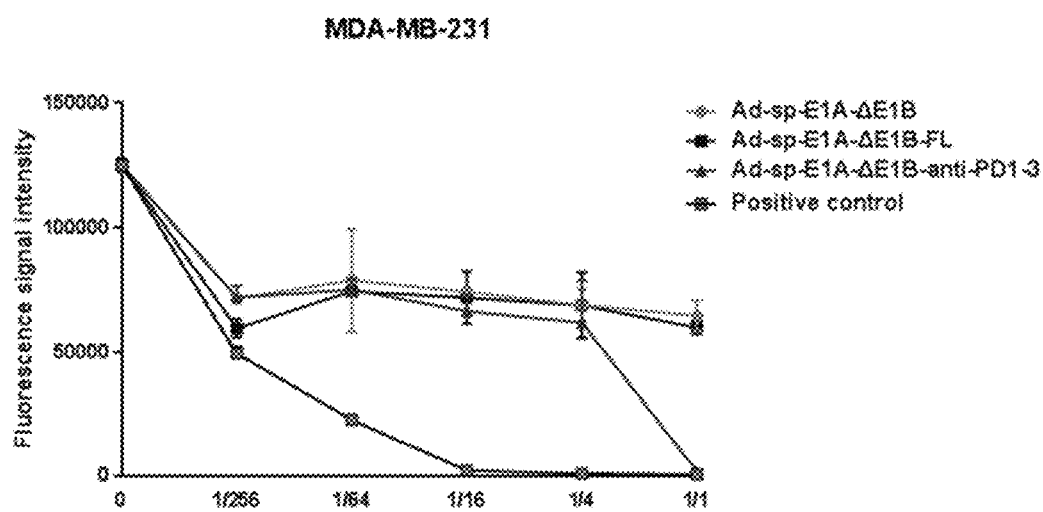

The results are shown in FIG. 5. PD1 antibodies with biological activity were present in the cell supernatants of both HCC827 cells and breast cancer cells MDA-MB-231 infected with recombinant oncolytic adenovirus Ad-sp-E1A-ΔE1B-anti-PD1-3, and its biological activity was stronger than the cell supernatant infected with recombinant oncolytic adenovirus Ad-sp-E1A-ΔE1B-FL (carrying PD1 full-length antibody).

Example 6

Figure 6:
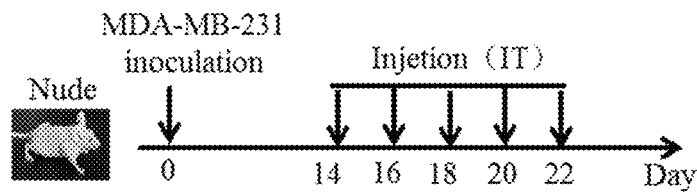
FIG. 6 shows the inhibitory effect of Ad-sp-E1A-ΔE1B-anti-PD1-3 on tumor growth of MDA-MB-231 transplanted tumor model in nude mouse.
Figure 6:
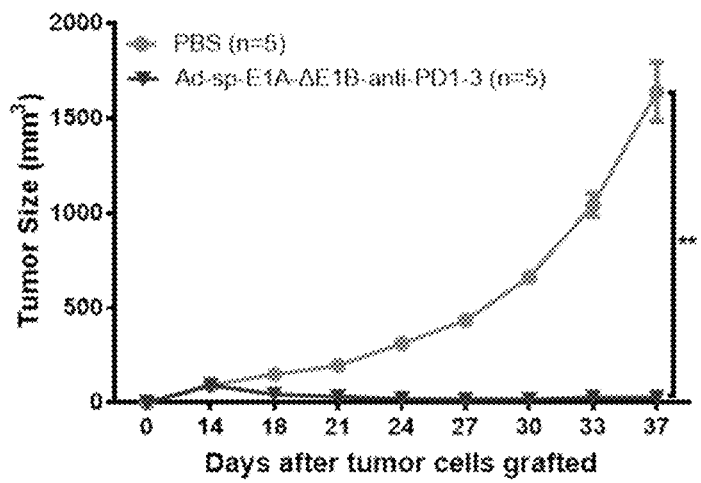
Figure 6:
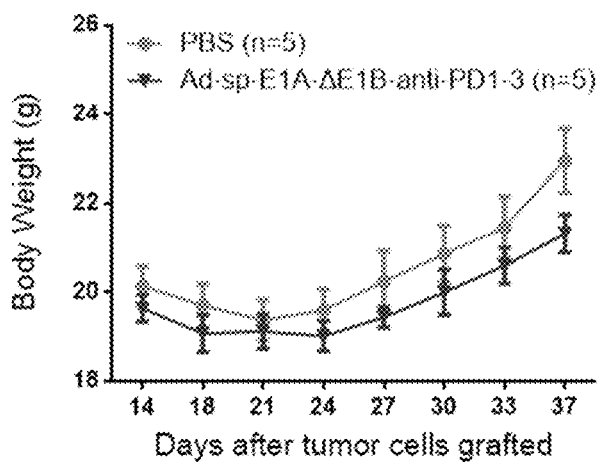

Recombinant Oncolytic Adenovirus Ad-sp-E1A-ΔE1B-anti-PD1-3 Significantly Inhibits the Growth of Xenograft Tumors in Nude Mice This example first tested the tumor suppression of Ad-sp-E1A-ΔE1B-anti-PD1-3 on the MDA-MB-231 (human breast cancer cells) xenograft tumor model in nude mouse. The experimental protocol is shown in FIG. 6A and the "Materials and Methods" section. The results are shown in FIG. 6B. The recombinant oncolytic adenovirus Ad-sp-E1A-ΔE1B-anti-PD1-3 can significantly inhibit the growth of MDA-MB-231 xenograft tumors in nude mice with a tumor inhibition rate ((the average tumor volume in the negative control group–the average tumor volume in the experimental group)/the average tumor volume in the negative control group*100%) up to 98.3%. In addition, during the experiment, the body weight of nude mice had the same changing trend in the negative control group and the experimental group, and there was no significant difference between the groups, which further showed that changes of tumor size (tumor cells) by the adenovirus were specific to tumors.

Figure 7:
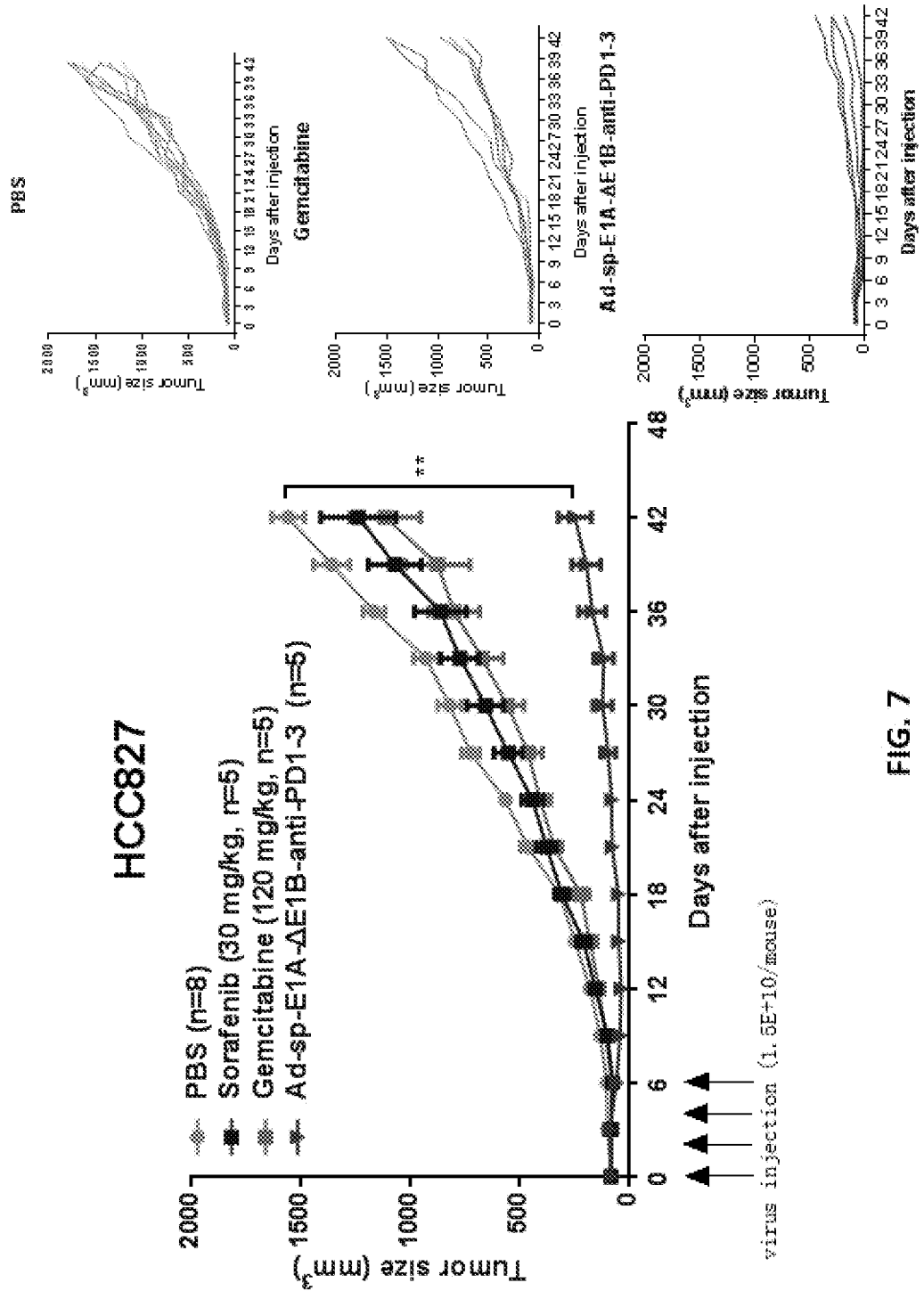
FIG. 7 shows the inhibitory effect of Ad-sp-E1A-ΔE1B-anti-PD1-3 on tumor growth of HCC827 transplanted tumor model in nude mouse.

Next, the tumor suppression activity of Ad-sp-E1A-ΔE1B-anti-PD1-3 on the HCC827 (human non-small cell lung cancer cell) xenograft tumor model in nude mice was also tested. The experimental protocol is shown in the "Materials and Methods" section. The results are shown in FIG. 7. The recombinant oncolytic adenovirus Ad-sp-E1A-ΔE1B-anti-PD1-3 can also significantly inhibit the growth of HCC827 xenograft tumors in nude mice, with a tumor inhibition rate up to 84.2%, which is significantly superior to that of the existing clinical drugs sorafenib and gemcitabine. In addition, during the experiment, the body weight change trend of each group of mice maintained the same, and there was no significant difference between the groups (data not shown).

Example 7

Figure 8:
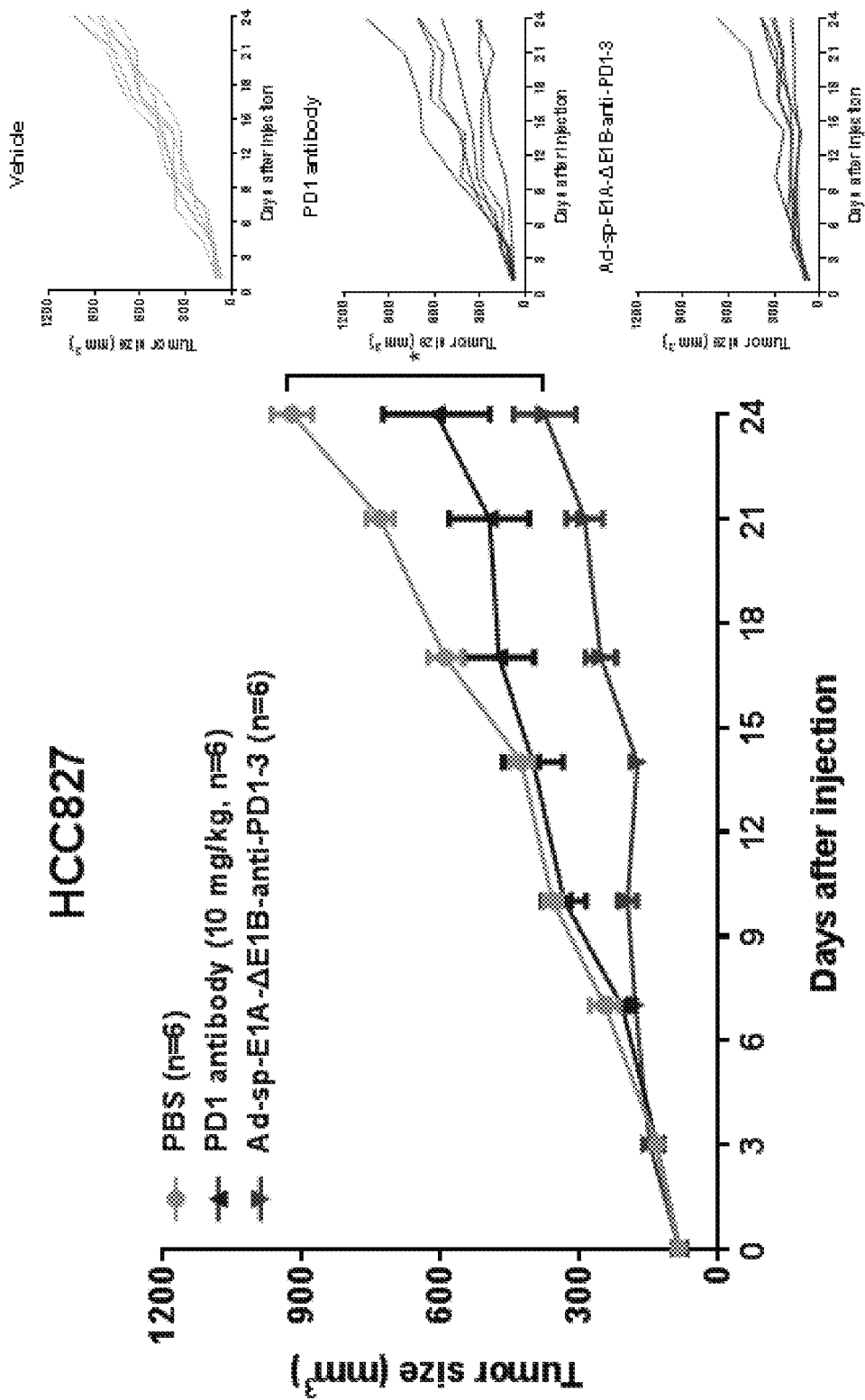
FIG. 8 shows the inhibitory effect of Ad-sp-E1A-ΔE1B-anti-PD1-3 on tumor growth of HCC827 transplanted tumor model in humanized mouse.

Recombinant Oncolytic Adenovirus Ad-sp-E1A-ΔE1B-anti-PD1-3 Significantly Inhibits the Growth of Xenograft Tumors in Humanized Mice This example tested the effect of Ad-sp-E1A-ΔE1B-anti-PD1-3 on tumor growth in the HCC827 xenograft tumors model in humanized mice with reconstructed human immune system. The results are shown in FIG. 8. The recombinant oncolytic adenovirus Ad-sp-E1A-ΔE1B-anti-PD1-3 can significantly inhibit the growth of HCC827 xenograft tumors, with a tumor inhibition rate up to 60.5%, which is significantly higher than that of PD1 antibody. In addition, during the experiment, the body weight change trend of each group of mice maintained the same, and there was no significant difference between the groups (data not shown).

The results of examples 6 and 7 showed that the recombinant oncolytic virus Ad-sp-E1A-ΔE1B-anti-PD1-3 also has a very excellent tumor suppressive effect in vivo. Especially in the humanized mice simulating the human immune system, it had a very high tumor inhibition rate, which also suggests that the recombinant oncolytic virus of the present disclosure is likely to have similar excellent effects in human. It can be seen that the recombinant oncolytic virus Ad-sp-E1A-ΔE1B-anti-PD1-3 has very good clinical application prospects.

What is claimed is:

1. An oncolytic virus comprising a nucleic acid encoding a PD-1 binding protein capable of inhibiting PD-1 activity, wherein the PD-1 binding protein is a fusion polypeptide comprising a PD-1 single-chain antibody and an immunoglobulin Fc fragment; and the fusion polypeptide has a structure of S-$V_L$-L-$V_H$-Fc;

S is an optional signal peptide sequence, and the signal peptide sequence is MDMRVPAQLLGLLLLWLP-GARC (SEQ ID NO: 14), or MDMRVPAQLLGLLLL-WFPGSRC (SEQ ID NO: 16);

$V_L$ is the light chain variable region of the PD-1 single-chain antibody, comprising CDR1 with sequence RAG-ONVONYLA (SEQ ID NO: 17), CDR2 with sequence NAQSLQT (SEQ ID NO: 18) and CDR3 with sequence QQYNSWPT (SEQ ID NO: 19);

L is a flexible linker comprising or mainly consisting of Ala (A), Thr (T), Gly (G) and/or Ser(S);

$V_H$ is the heavy chain variable region of the PD-1 single-chain antibody, comprising CDR1 with sequence GFSLSTSGT (SEQ ID NO: 20), CDR2 with sequence CWEDS (SEQ ID NO: 21) and CDR3 with sequence EDSGYFWFPY (SEQ ID NO: 22); and Fc is an immunoglobulin Fc fragment, wherein the Fc fragment is derived from the Fc fragment of IgG, IgA, IgD, IgE or IgM.

2. The oncolytic virus according to claim 1, wherein the virus is an adenovirus.

3. The oncolytic virus according to claim 2, wherein the virus comprises E1A gene driven by a survivin promoter, and the endogenous promoter of the E1A gene in viral genome is replaced by the survivin promoter; and/or the activity of E1B gene is reduced or completely inactivated.

4. The oncolytic virus according to claim 1, wherein the nucleic acid is operably linked to a promoter.

5. The oncolytic virus according to claim 1, wherein the oncolytic virus was deposited at China Center for Type Culture Collection on Aug. 21, 2018, under the accession number CCTCC NO: V201853.

6. A pharmaceutical composition comprising a pharmaceutically effective amount of the oncolytic virus according to claim 1, and optionally a pharmaceutically acceptable carrier.

7. The pharmaceutical composition according to claim 6, wherein the pharmaceutical composition is formulated for oral, nebulized inhalation, intravenous, intramuscular, subcutaneous, perfusion, intralesional injection, or intratumoral administration.

8. The pharmaceutical composition according to claim 6, comprising the oncolytic virus in an amount of about $10^8$ vp to $10^{12}$ vp.

9. A method of treating a proliferative tumor disease, comprising administering the oncolytic virus according to claim 1 to a subject in need thereof, wherein the tumor is selected from the group consisting of prostate cancer, breast cancer, colorectal cancer, lung cancer, liver cancer, melanoma, head and neck cancer, lymphoma, gastric cancer, esophageal cancer, ovarian cancer, head and neck squamous cell carcinoma, bladder cancer, and kidney cancer.

10. The method according to claim 9, wherein the oncolytic virus is administered to the subject in an amount of about $10^8$ vp to $10^{12}$ vp by oral, nebulized inhalation, intravenous, intramuscular, subcutaneous, perfusion, intralesional injection, or intratumoral administration, with an administration number of 1-6, and an administration interval of every 1, 2, 3, 4, 5, 6, 7 or more days, or 1, 2, 3, 4, 5, 6 or more times over the course of one day.

11. The oncolytic virus according to claim 3, wherein E1B gene is knocked out from the viral genome.

12. The oncolytic virus according to claim 1, wherein the amino acid sequence of the light chain variable region is shown in SEQ ID NO: 4 and the amino acid sequence of the heavy chain variable region is shown in SEQ ID NO: 3.

13. The oncolytic virus according to claim 1, wherein L is 1-50 amino acids in length.

14. The oncolytic virus according to claim 1, wherein L is (Gly4Ser) m, and m is a natural number between 1 and 10.

15. The oncolytic virus according to claim 1, wherein L is $(Gly_4Ser)_6$ or L is $A(EAAAK)_nA$, and n is a natural number between 1 and 9.

16. The oncolytic virus according to claim 1, wherein the Fc fragment is derived from the Fc fragment of IgG.

17. The oncolytic virus according to claim 1, wherein the sequence of the Fc fragment is shown in SEQ ID NO: 9.

18. The oncolytic virus according to claim 4, wherein the promoter is a CMV promoter.

* * * * *